United States Patent
Wilson et al.

(10) Patent No.: US 12,193,903 B2
(45) Date of Patent: Jan. 14, 2025

(54) COMPOSITE MATERIALS INCLUDING CERAMIC FIBERS AND NANOCLUSTERS, DENTAL PRODUCTS, KITS, AND METHODS OF MAKING AND USING SAME

(71) Applicant: Solventum Intellectual Properties Company, Maplewood, MN (US)

(72) Inventors: David M. Wilson, Bloomington, MN (US); Bradley D. Craig, Lake Elmo, MN (US); Mark B. Agre, Rochester, MN (US); Kari A. McGee, New Brighton, MN (US); Daimon K Heller, Houlton, WI (US); William V. Chiu, Woodbury, MN (US); Gareth A. Hughes, St. Paul, MN (US)

(73) Assignee: Solventum Intellectual Properties Company, Maplewood, MN (US)

( * ) Notice: Subject to any disclaimer, the term of this patent is extended or adjusted under 35 U.S.C. 154(b) by 755 days.

(21) Appl. No.: 17/267,574

(22) PCT Filed: Sep. 6, 2019

(86) PCT No.: PCT/IB2019/057531
§ 371 (c)(1),
(2) Date: Feb. 10, 2021

(87) PCT Pub. No.: WO2020/053723
PCT Pub. Date: Mar. 19, 2020

(65) Prior Publication Data
US 2021/0315664 A1 Oct. 14, 2021

Related U.S. Application Data

(60) Provisional application No. 62/731,215, filed on Sep. 14, 2018.

(51) Int. Cl.
*C08J 5/00* (2006.01)
*A61C 5/20* (2017.01)
(Continued)

(52) U.S. Cl.
CPC .................. *A61C 5/20* (2017.02); *A61K 6/17* (2020.01); *A61K 6/802* (2020.01); *A61K 6/829* (2020.01);
(Continued)

(58) Field of Classification Search
CPC . C08J 5/0405; C08J 5/005; C08J 5/043; C08J 2335/02; A61K 6/17; A61K 6/802; A61K 6/836
(Continued)

(56) References Cited

U.S. PATENT DOCUMENTS 3,066,112 A 11/1962 Bowen
3,117,099 A 1/1964 Proops
(Continued)

FOREIGN PATENT DOCUMENTS

CN 109464287 3/2019
EP 0173567 3/1986
(Continued)

OTHER PUBLICATIONS

Adamson, "Aminoalkyl Tertiary Carbinols and Derived Products. Part I. 3-Amino-1 : 1—diphenylpropan-1-ols", Journal of the Royal Society of Chemistry, 1949, pp. S144-S152.
(Continued)

*Primary Examiner* — Ruiyun Zhang

(57) ABSTRACT

The present disclosure provides a composite material. The composite material includes 20 to 40 weight percent (wt. %) of a polymerizable component; 6 to 40 wt. % of ceramic fibers; and 30 to 70 wt. % of nanoclusters. Each of the ceramic fibers has a diameter and a length, the ceramic fibers
(Continued)

having an arithmetic mean diameter of 0.3 micrometers to 5 micrometers, and the length of fifty percent of the ceramic fibers (based on a total number of the ceramic fibers) is at least 10 micrometers and the length of ninety percent of the ceramic fibers is no greater than 500 micrometers. The present disclosure also provides a method of making the composite material. The method includes obtaining components and admixing the components to form a composite material. Further, the present disclosure provides a method of using a composite material including placing a composite material near or on a tooth surface, changing the shape of the composite material near or on a tooth surface, and hardening the composite material. In addition, the present disclosure provides dental products and kits. Hardened composite materials can exhibit high strength.

20 Claims, 2 Drawing Sheets

(51) Int. Cl.
    *A61K 6/17*        (2020.01)
    *A61K 6/802*      (2020.01)
    *A61K 6/829*      (2020.01)
    *A61K 6/836*      (2020.01)
    *C08F 222/10*     (2006.01)
    *C08F 222/22*     (2006.01)
    *C08J 5/04*        (2006.01)

(52) U.S. Cl.
    CPC ........ *A61K 6/836* (2020.01); *C08F 222/1067* (2020.02); *C08F 222/22* (2013.01); *C08J 5/005* (2013.01); *C08J 5/0405* (2021.05); *C08J 5/043* (2013.01); *C08F 2800/20* (2013.01); *C08J 2335/02* (2013.01)

(58) Field of Classification Search
    USPC .................................................. 523/115, 116
    See application file for complete search history.

(56) References Cited

U.S. PATENT DOCUMENTS

| | | |
|---|---|---|
| 3,539,533 A | 11/1970 | Lee, II |
| 3,629,187 A | 12/1971 | Waller |
| 3,708,296 A | 1/1973 | Schlesinger |
| 3,709,866 A | 1/1973 | Waller |
| 3,751,399 A | 8/1973 | Lee |
| 3,766,132 A | 10/1973 | Lee |
| 3,860,556 A | 1/1975 | Taylor |
| 4,002,669 A | 1/1977 | Gross |
| 4,047,965 A | 9/1977 | Karst |
| 4,069,055 A | 1/1978 | Crivello |
| 4,115,346 A | 9/1978 | Gross |
| 4,216,288 A | 8/1980 | Crivello |
| 4,250,311 A | 2/1981 | Crivello |
| 4,259,117 A | 3/1981 | Yamauchi |
| 4,292,029 A | 9/1981 | Craig |
| 4,298,738 A | 11/1981 | Lechtken |
| 4,308,190 A | 12/1981 | Walkowiak |
| 4,324,744 A | 4/1982 | Lechtken |
| 4,327,014 A | 4/1982 | Kawahara |
| 4,356,296 A | 10/1982 | Griffith |
| 4,379,695 A | 4/1983 | Orlowski |
| 4,385,109 A | 5/1983 | Lechtken |
| 4,387,240 A | 6/1983 | Berg |
| 4,404,150 A | 9/1983 | Tsunekawa |
| 4,503,169 A | 3/1985 | Randklev |
| 4,642,126 A | 2/1987 | Zador |
| 4,648,843 A | 3/1987 | Mitra |
| 4,652,274 A | 3/1987 | Boettcher |
| 4,665,217 A | 5/1987 | Reiners |
| 4,695,251 A | 9/1987 | Randklev |
| 4,710,523 A | 12/1987 | Lechtken |
| 4,737,593 A | 4/1988 | Ellrich |
| 4,752,338 A | 6/1988 | Reiners |
| 4,985,340 A | 1/1991 | Palazzotto |
| 5,026,902 A | 6/1991 | Fock |
| 5,076,844 A | 12/1991 | Fock |
| 5,084,586 A | 1/1992 | Farooq |
| 5,089,536 A | 2/1992 | Palazzotto |
| 5,124,417 A | 6/1992 | Farooq |
| 5,425,640 A | 6/1995 | Scharf |
| 5,545,676 A | 8/1996 | Palazzotto |
| 5,856,373 A | 1/1999 | Kaisaki |
| 5,861,445 A | 1/1999 | Xu |
| 5,998,549 A | 12/1999 | Milbourn |
| 6,025,406 A | 2/2000 | Oxman |
| 6,030,606 A | 2/2000 | Holmes |
| 6,251,963 B1 | 6/2001 | Köhler |
| 6,270,562 B1 | 8/2001 | Jia |
| 6,306,926 B1 | 10/2001 | Bretscher |
| 6,334,775 B2 | 1/2002 | Xu |
| 6,376,590 B2 | 4/2002 | Kolb |
| 6,387,981 B1 | 5/2002 | Zhang |
| 6,572,693 B1 | 6/2003 | Wu |
| 6,730,156 B1 | 5/2004 | Windisch |
| 6,765,036 B2 | 7/2004 | Dede |
| 6,872,076 B2 | 3/2005 | Karmaker |
| 6,899,948 B2 | 5/2005 | Zhang |
| 7,022,173 B2 | 4/2006 | Cummings |
| 7,030,049 B2 | 4/2006 | Rusin |
| 7,085,063 B2 | 8/2006 | Magarill |
| 7,090,721 B2 | 8/2006 | Craig |
| 7,090,722 B2 | 8/2006 | Budd |
| 7,156,911 B2 | 1/2007 | Kangas |
| 7,160,528 B2 | 1/2007 | Rusin |
| 7,361,216 B2 | 4/2008 | Kangas |
| 7,393,882 B2 | 7/2008 | Wu |
| 7,429,422 B2 | 9/2008 | Davidson |
| 7,649,029 B2 | 1/2010 | Kolb |
| 8,647,510 B2 | 2/2014 | Kolb |
| 8,785,513 B2 | 7/2014 | Lassila |
| 2010/0089286 A1 | 4/2010 | Craig |
| 2011/0196062 A1 | 8/2011 | Craig |
| 2012/0129970 A1 | 5/2012 | Li |
| 2013/0023600 A1 | 1/2013 | Kobashigawa |
| 2018/0028413 A1 | 2/2018 | Craig |
| 2018/0221250 A1 | 8/2018 | Qiu |

FOREIGN PATENT DOCUMENTS

| | | |
|---|---|---|
| GB | 2291053 | 1/1996 |
| WO | WO 1990-008799 | 8/1990 |
| WO | 1999/20225 A2 | 4/1999 |
| WO | WO 2000-038619 | 7/2000 |
| WO | WO 2000-042092 | 7/2000 |
| WO | WO 2001-007444 | 2/2001 |
| WO | WO 2001-092271 | 12/2001 |
| WO | WO 2003-063804 | 8/2003 |
| WO | WO 2008-000917 | 1/2008 |
| WO | WO 2015-197679 | 12/2015 |
| WO | WO 2016-140950 | 9/2016 |
| WO | WO 2018-169704 | 9/2018 |

OTHER PUBLICATIONS

International Search Report for PCT International Application No. PCT/IB2019/057531, mailed on Dec. 17, 2019, 3 pages.
Olson, "Particle Shape Factors and Their Use in Image Analysis—Part 1: Theory", Journal of GXP Compliance, vol. 15, No. 3, Jan. 1, 2011, pp. 85-96.

COMPOSITE MATERIALS INCLUDING CERAMIC FIBERS AND NANOCLUSTERS, DENTAL PRODUCTS, KITS, AND METHODS OF MAKING AND USING SAME

CROSS REFERENCE TO RELATED APPLICATIONS

This application is a national stage filing under 35 U.S.C. 371 of PCT/IB2019/057531, filed Sep. 6, 2019, which claims the benefit of U.S. Application No. 62/731,215, filed Sep. 14, 2018, the disclosure of which is incorporated by reference in their entirety herein.

TECHNICAL FIELD

The present disclosure broadly relates to composite materials, and more particularly composite materials containing ceramic fibers.

BACKGROUND

Direct dental restorative materials consist of a curable phase, typically a methacrylate resin, an initiator and a filler system. These materials are typically highly filled with particulate such as nanoscale particles, micrometer milled materials and/or solution grown inorganics. Furthermore, similar compositions made from pre-cured "composites" (e.g., dental mill blanks) have been introduced to the market, where the material is cured out of the mouth and shaped into a final restorative shape (e.g., inlay, onlay or crown) via a reduction process (e.g., milling). All of these dental restorative materials have requirements that include high strength, stiffness, and fracture toughness to function in the oral environment. Especially in large posterior restorations, a higher fracture toughness material is highly desirable.

Attempts have been made to include fibers in dental restorative materials in order to improve their mechanical properties. However, this has come at a cost to handling and aesthetic characteristics. The use of fibers unfortunately creates a stiff, "crunchy" type of handling that is difficult to work with (e.g., shape, and feather). Once cured, the surfaces of these dental restorative materials rapidly lose their gloss with every day wear. Additionally, many of these dental restorative materials produce a highly opaque material due to refractive index mismatch between the fiber and the resin. This refractive index mismatch results in a less than desirable aesthetic result.

As such, there is a need in the art for a composite material that includes fibers, where the composite material is easy to handle and provides good aesthetics properties while still providing the necessary mechanical properties for use as a dental restorative material.

SUMMARY

The present disclosure provides a composite material having improved handling properties along with good aesthetic qualities while still providing the necessary mechanical properties for use as a dental restorative material. More specifically, in a first aspect, a composite material is provided. The composite material includes 20 to 40 weight percent (wt. %) of a polymerizable component; 6 to 40 wt. % of ceramic fibers; and 30 to 70 wt. % of nanoclusters. The wt. % values of the composite material are based on a total weight of the composite material and total to a value of 100 wt. %. Each of the ceramic fibers has a diameter and a length, the ceramic fibers have an arithmetic mean diameter of 0.3 micrometers to 5 micrometers, and the length of fifty percent of the ceramic fibers, based on a total number of the ceramic fibers, is at least 10 micrometers and the length of ninety percent of the ceramic fibers, based on the total number of the ceramic fibers, is no greater than 500 micrometers.

In a second aspect, a dental product is provided. The dental product is made by hardening the composite material according to the first aspect.

In a third aspect, a method of making a composite material is provided. The method includes obtaining a plurality of components and admixing the plurality of components to make the composite material. The components include 20 to 40 wt. % of a polymerizable component; 6 to 40 wt. % of ceramic fibers; and 30 to 70 wt. % of nanoclusters. The wt. % values of the composite material are based on a total weight of the composite material and total to a value of 100 wt. %. Each of the ceramic fibers has a diameter and a length, the ceramic fibers have an arithmetic mean diameter of 0.3 micrometers to 5 micrometers, and the length of fifty percent of the ceramic fibers, based on a total number of the ceramic fibers, is at least 10 micrometers and the length of ninety percent of the ceramic fibers, based on the total number of the ceramic fibers, is no greater than 500 micrometers.

In a fourth aspect, a method of using a composite material is provided. The method includes placing the composite material according to the first aspect near or on a tooth surface; changing the shape of the composite material near or on the tooth surface; and hardening the composite material.

In a fifth aspect, a kit is provided. The kit includes a composite material according to the first aspect; and at least one container to hold the composite material.

Composite materials according to at least certain embodiments of the present disclosure can provide hardened composite materials (e.g., dental products) exhibiting good strength, good polish retention, wear rate, and/or visual appearance.

The above summary of the present disclosure is not intended to describe each disclosed embodiment or every implementation of the present disclosure. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

Figure 1:
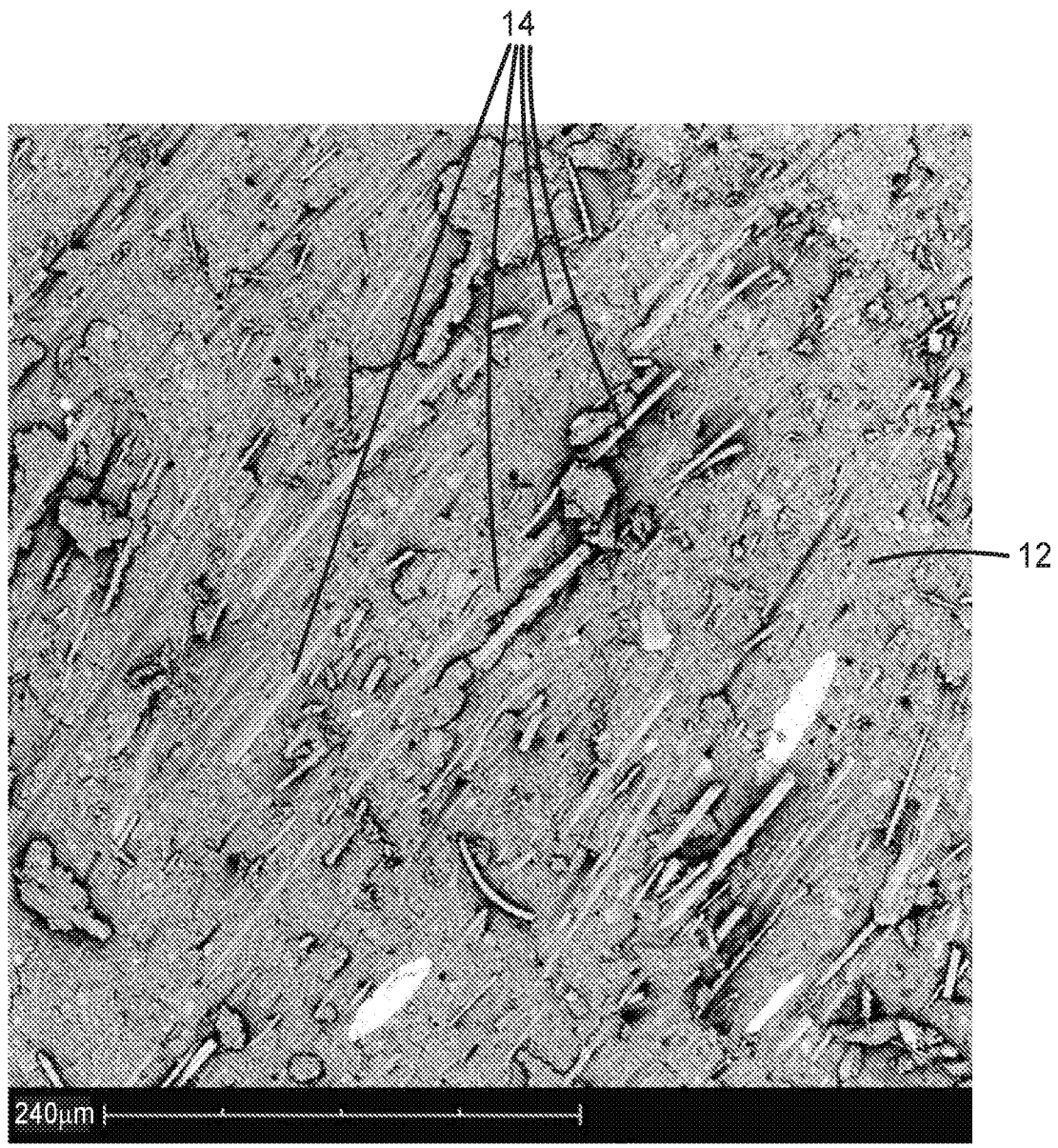
FIG. 1 is a scanning electron microscopy (SEM) micrograph of a diametral tensile strength (DTS) fracture surface of a hardened composite material according to the present disclosure.

While the above-identified figures set forth several embodiments of the disclosure other embodiments are also contemplated, as noted in the description. The figures are not necessarily drawn to scale. In all cases, this disclosure presents the invention by way of representation and not limitation. It should be understood that numerous other modifications and embodiments can be devised by those skilled in the art, which fall within the scope and spirit of the principles of the invention.

DETAILED DESCRIPTION OF ILLUSTRATIVE EMBODIMENTS

The present disclosure provides a composite material having improved handling properties along with good aesthetic qualities while still providing the necessary mechanical properties for use as a dental restorative material. Specifically, the composite material includes a polymerizable component, ceramic fibers and nanoclusters. The ceramic fibers used in the composite material, as discussed herein, have a small diameter. The small diameter of the ceramic fibers along with the use of the nanoclusters surprisingly results in improvements to both the handling properties of the composite material and upon hardening the aesthetics properties of the hardened composite material. Examples of such improved aesthetics properties include hardened composite materials that are able to retain their polish even after exposure to repetitive abrasion, such as through brushing with toothpaste.

The hardened composite material of the present disclosure may also have other desirable aesthetic, physical and mechanical properties. For example, the hardened composite material of the present disclosure can have radiopacity, high mechanical strength and a substantial translucency. Radiopacity is a very desirable property for a composite material used in dental applications. Being radiopaque allows the composite material to be examined using standard dental X-ray equipment, thereby facilitating long term detection of marginal leakage or caries in tooth tissue adjacent to the hardened composite material.

The hardened composite material can have a substantial translucency (e.g., a low visual opacity) to visible light. Having translucency is desirable so that the hardened composite material will have a life-like appearance when used as a dental restorative material. If such a composite material is intended to be hardened or polymerized using visible light-induced photoinitiation, translucency is desirable in order to reach the depth of cure required (sometimes as much as two millimeters or more), to accomplish uniform hardness in the hardened composite material, and to respond to the physical limitations imposed by carrying out the hardening reaction within the mouth (which require, among other things, that the unhardened composite material usually be exposed to light from limited angles, and that the hardening radiation be provided by a portable instrument). The translucency can be achieved for the composite material, as discussed herein, in part by matching the refractive index of the ceramic fibers with the refractive index of the hardened polymerizable component of the composite material.

Practitioners also desire good handling properties in a composite material used for dental applications, as this property translates to time savings. For example, in dental restorative work, it is desirable that the composite material be easily shaped, contoured and feathered into the desired shape. Until the present disclosure, attempts at using fibers in composite materials at loadings levels sufficient to improve the mechanical properties made the handling of the composite material poor at best. Such attempts with ground or milled fibers created a "crunchy" type of handling, which is something to avoid for a dental restorative material to have good handling and "featherability" characteristics. These other composite materials also had "lumps," which makes for unpredictable and non-uniform handling of the material.

Unlike these failed attempts, the composite material of the present disclosure maintains good handling characteristics at fiber loadings sufficient to improve the mechanical properties. The composite material of the present disclosure displays a consistent and uniform composition, which allows for predictable and uniform handling of the composite material. In addition, the refractive index of the ceramic fibers and the polymerizable component used in the present disclosure are suitably matched so as to provide substantial translucency (e.g., low visual opacity) and high aesthetic quality for use as a dental restorative material. Finally, the hardened composite material of the present disclosure displays enhanced fracture toughness and flexural strength due to the presence of the ceramic fibers and the nanoclusters, with minimal degradation of handling or aesthetic properties of the composite material. This is unexpected, as the use of fibers is known to decrease both handling and aesthetic properties of composite materials.

While not wishing to be bound by theory, it is hypothesized that it is a combination of the ceramic fiber diameter size and relatively uniform distribution of the ceramic fibers and the nanoclusters used in the composite material of the present disclosure that is leading to these favorable attributes. The specific diameter range of the ceramic fibers surprisingly results in improvements to both the handling properties of the composite material and upon hardening the physical properties of the hardened composite material. Examples of such improved physical properties include dental restorative materials that are able to retain their polish after repetitive abrasive contact.

Glossary

The term "amorphous material" refers to material derived from a melt and/or a vapor phase that lacks long range crystal structure as determined by X-ray diffraction and/or has an exothermic peak corresponding to the crystallization of the amorphous material as determined by a DTA (differential thermal analysis) as determined by the test described herein entitled "Differential Thermal Analysis".

The term "ceramic" includes amorphous material, glass, crystalline ceramic, glass-ceramic, and combinations thereof.

The term "crystalline ceramic" refers to a ceramic material exhibiting a discernible X-ray powder diffraction pattern.

The term "glass" refers to amorphous material exhibiting a glass transition temperature.

The term "glass-ceramic" refers to ceramics comprising crystals formed by heat-treating amorphous material.

The term "electron donor" generally refers to a compound that has a substituent that can donate electrons. Suitable examples include, but are not limited to, a primary amino, secondary amino, tertiary amino, hydroxy, alkoxy, aryloxy, alkyl, or combinations thereof.

As used herein, "hardenable" is descriptive of a material or composition that can be cured (e.g., polymerized or crosslinked) or solidified, for example, by removing solvent (e.g., by evaporation and/or heating); heating to induce polymerization and/or crosslinking; irradiating to induce polymerization and/or crosslinking; and/or by mixing one or more components to induce polymerization and/or crosslinking. "Hardened" refers to a material or composition that has been cured (e.g., polymerized or crosslinked).

By "dental product" is meant an article that can be adhered (e.g., bonded) to an oral surface (e.g., a tooth structure). Typically, a dental product is a restored dentition or a portion thereof. Examples include restoratives, replacements, inlays, onlays, veneers, full and partial crowns, bridges, implants, implant abutments, copings, anterior fillings, posterior fillings, cavity liners, sealants, dentures, posts, bridge frameworks and other bridge structures, abutments, orthodontic appliances and devices, and prostheses (e.g., partial or full dentures).

As used herein, "sizing" is defined as starch, oil, wax or other suitable ingredients (e.g., an organic ingredient) applied to a fiber strand to protect and aid handling. A sizing contains ingredients to provide lubricity and binding action. Sizing may also encompass surface treatments, for example with a silane, where the silane may include a reactive group, for example a polymerizable group.

By "oral surface" is meant a soft or hard surface in the oral environment. Hard surfaces typically include tooth structure including, for example, natural and artificial tooth surfaces, bone, tooth models, dentin, enamel, cementum, and the like By "filler" is meant a particulate material suitable for use in the oral environment. Dental fillers generally have a number average particle size diameter of at most 100 micrometers.

By "contouring" refers to the process of shaping a material (using dental instruments) so that it resembles the natural dental anatomy. For easy contouring, materials should have a sufficiently high viscosity that they maintain their shape after manipulation with a dental instrument, and yet the viscosity should not be so high that it is difficult to shape the material.

By "feathering" refers to the process of reducing the dental restorative material to a thin film in order to blend the material into the natural dentition. This is done with a dental instrument at the margin of the manipulated material and the natural dentition.

As used herein, "nanoparticles" are discrete non-fumed metal oxide nanoparticles. Discrete non-fumed metal oxide nanoparticles can be further classified as either "discrete non-fumed non-heavy metal oxide nanoparticles" or "discrete non-fumed heavy metal oxide nanoparticles." The "discrete non-fumed non-heavy metal oxide nanoparticles" means an oxide of elements other than those of heavy metals (which are defined herein as the "discrete non-fumed heavy metal oxide nanoparticles"). As used herein, "non-heavy metal oxide" means a metal oxide of elements having an atomic number of no greater than 28. In one aspect of the disclosure, silica is an example of a non-heavy metal oxide and silica nanoparticles are an example of discrete non-fumed non-heavy metal oxide nanoparticles. As used herein, "heavy metal oxide" means an oxide of elements having an atomic number greater than 28. In one aspect of the disclosure, zirconium oxide is an example of the heavy metal oxide. The average particle size of nanoparticles can be determined by cutting a thin sample of hardened dental composition and measuring the particle diameter of about 50-100 particles using a transmission electron micrograph at a magnification of 300,000 and calculating the average.

As used herein, "discrete" means unaggregated, individual particles (e.g., nanoparticles) that are separate from each other.

As used herein, a "nanocluster" generally refers to a group of two or more nanoparticles associated by relatively weak, but sufficient intermolecular forces that cause the nanoparticles to clump to together, even when dispersed in a hardenable resin. Preferred nanoclusters can comprise loosely aggregated substantially amorphous cluster of discrete non-fumed non-heavy metal oxide nanoparticles (e.g., silica nanoparticles) and heavy metal oxide (e.g., zirconia). Where zirconia is present as the heavy metal oxide, the zirconia can be crystalline or amorphous. Furthermore, the heavy metal oxide can be present as particles (e.g., discrete non-fumed heavy metal oxide nanoparticles such as zirconia nanoparticles). The particles from which the nanocluster is formed preferably have an average diameter of 5 nm to about 100 nm. However, the average particle size of the loosely aggregated nanocluster is typically considerably larger. Typically, the nanoclusters have a longest dimension in the micrometer range (e.g., 3 micrometers, 5 micrometers, 7 micrometers, 10 micrometers, and in some cases, 30 to 50 micrometers). Nanocluster size may be determined according to the methods generally described in U.S. Pat. No. 6,730,156 (Windisch, et al.) (column 21, lines 1-22, "Cluster Size Determination").

By "substantially amorphous" it is meant that the nanoclusters are essentially free of crystalline structure. Absence of crystallinity (or presence of amorphous phases) is preferably determined by a procedure that provides a Crystallinity Index, as generally described in U.S. Pat. No. 6,730,156 (Windisch, et al.) (column 21, lines 23 to column 22, line 33, "Crystallinity Index Procedure"). The Crystallinity Index characterizes the extent a material is crystalline or amorphous, whereby a value of 1.0 is indicative of a fully crystalline structure, and a value near zero indicates presence of amorphous phase only. The nanoclusters of the present disclosure preferably have an index of less than about 0.1; more preferably less than about 0.05.

By "nano" is meant a material in a form having at least one dimension that is, on average, at most 200 nanometers (e.g., discrete non-fumed metal oxide nanoparticles). Thus, nano materials refer to materials including, for example, nanoparticles and nanoclusters, as defined herein. So, for example, "nanoparticles" refers to particles having a number average diameter of at most 200 nanometers. As used herein for a spherical particle, "size" refers to the diameter of the particle. As used herein for a non-spherical particle, "size" refers to the longest dimension of the particle. In certain embodiments, the nanoparticles are comprised of discrete, non-aggregated and non-agglomerated particles.

As used herein, the term "ethylenically unsaturated compound" is meant to include monomers, oligomers, and polymers having at least one ethylenic unsaturation.

By "polymerization" is meant the forming of a higher weight material from monomers or oligomers. The polymerization reaction also can involve a cross-linking reaction.

As used herein, the term "(meth)acrylate" is a shorthand reference to acrylate, methacrylate, or combinations thereof, and "(meth)acrylic" is a shorthand reference to acrylic, methacrylic, or combinations thereof. As used herein, "(meth)acrylate-functional compounds" are compounds that include, among other things, a (meth)acrylate moiety.

As used herein a "hardened composite material" is the composite material of the present disclosure that has undergone a physical and/or a chemical transformation to produce a solid and firm composite material that is resistant to pressure. The physical and/or chemical transformation of the composite material can be due to a setting, curing, polymerizing, crosslinking or a fusing process.

As used herein "translucency" is the degree to which a material transmits light. This may be quantified by contrast ratio, translucency parameter, or percent transmittance through a known thickness of material. Translucency in dental restorative materials is often determined from the contrast ratio. The contrast ratio is the ratio of white light remission from a specimen placed over a standardized black background ($R_b$) and a standardized white background ($R_w$). The contrast ratio is calculated as $CR = R_b/R_w \times 100$. A contrast ratio of 100 represents a completely opaque specimen. Translucency is expressed as 100-CR.

As used herein a "dental mill blank" is a block of material (e.g., hardened composite material) from which dental product can be milled.

By "machining" is meant milling, grinding, cutting, carving, or shaping a material having a three dimensional structure or shape by a machine.

As used herein, "CAD/CAM" is the abbreviation for computer-aided design/computer-aided manufacturing.

In the present disclosure, weight percentage (wt. %) values of the various components (e.g., at least a polymerizable component, ceramic fibers and nanoclusters) that make up the composite material are recited. These wt. % values of the composite material are based on a total weight of the composite material and the wt. % values of all the components that are used to form the composite material of the present disclosure always total to a value of 100 wt. %.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

In this application, terms such as "a", "an", and "the" are not intended to refer to only a singular entity, but include the general class of which a specific example may be used for illustration. The terms "a", "an", and "the" are used interchangeably with the term "at least one." The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise.

The term "and/or" means one or all of the listed elements or a combination of any two or more of the listed elements.

Also herein, all numbers are assumed to be modified by the term "about" and preferably by the term "exactly." As used herein in connection with a measured quantity, the term "about" refers to that variation in the measured quantity as would be expected by the skilled artisan making the measurement and exercising a level of care commensurate with the objective of the measurement and the precision of the measuring equipment used. Also herein, the recitations of numerical ranges by endpoints include all numbers subsumed within that range as well as the endpoints (e.g., 1 to 5 includes 1, 1.5, 2, 2.75, 3, 3.80, 4, 5, etc.).

As used herein as a modifier to a property or attribute, the term "generally", unless otherwise specifically defined, means that the property or attribute would be readily recognizable by a person of ordinary skill but without requiring absolute precision or a perfect match (e.g., within +/−20% for quantifiable properties). The term "substantially", unless otherwise specifically defined, means to a high degree of approximation (e.g., within +/−10% for quantifiable properties) but again without requiring absolute precision or a perfect match. Terms such as same, equal, uniform, constant, strictly, and the like, are understood to be within the usual tolerances or measuring error applicable to the particular circumstance rather than requiring absolute precision or a perfect match.

In a first aspect, a composite material is provided. The composite material includes 20 to 40 weight percent (wt. %) of a polymerizable component; 6 to 40 wt. % of ceramic fibers; and 30 to 70 wt. % of nanoclusters. The wt. % values of the composite material are based on a total weight of the composite material and total to a value of 100 wt. %. Each of the ceramic fibers has a diameter and a length, the ceramic fibers have an arithmetic mean diameter of 0.3 micrometers to 5 micrometers, and the length of fifty percent of the ceramic fibers, based on a total number of the ceramic fibers, is at least 10 micrometers and the length of ninety percent of the ceramic fibers, based on the total number of the ceramic fibers, is no greater than 500 micrometers.

It has been discovered that the incorporation of ceramic fibers having a certain range of diameters enhances the strength of hardened composite materials according to the present disclosure as well as providing good polish retention and visual appearance. More particularly, the ceramic fibers have an arithmetic mean diameter (i.e., the sum of the diameters of a group of fibers divided by the number of fibers in the group) of 0.3 micrometers to 5 micrometers, such as 0.3 micrometers to 3 micrometers or 2 micrometers to 5 micrometers. For instance, the ceramic fibers may have an arithmetic mean diameter of 0.3 micrometers or more, 0.4 micrometers or more, 0.5 micrometers or more, 0.6 micrometers or more, 0.7 micrometers or more, 0.8 micrometers or more, 0.9 micrometers or more, 1.0 micrometers or more, 1.25 micrometers or more, 1.5 micrometers or more, 1.75 micrometers or more, 2.0 micrometers or more, 2.25 micrometers or more, 2.5 micrometers or more, or 2.75 micrometers or more; and 5.0 micrometers or less, 4.75 micrometers or less, 4.5 micrometers or less, 4.25 micrometers or less, 4.0 micrometers or less, 3.75 micrometers or less, 3.5 micrometers or less, 3.25 micrometers or less, or 3.0 micrometers or less. The diameter is measured using scanning electron microscopy (SEM), in which the diameter of at least 50 (e.g., 50-100) individual ceramic fibers is measured and the arithmetic mean is calculated from all the measured diameters. It is appreciated that in addition to a circular cross-section for the ceramic fibers, it is also possible to have different cross-sectional shapes. Examples include, but are not limited to, ribbon like, oval (non-circular) and polygonal (e.g., triangular or square), among others known in the art.

The ceramic fibers of the composite material also each have a length. As each of the ceramic fibers can have a different length, the lengths of the ceramic fibers can be grouped into percentages of a total number of the ceramic fibers that are either above or below a given length value. For example, the ceramic fiber length "L" is giving by the fraction of the ceramic fibers that are either shorter or longer than a given value. So, for example, "L50" can denote that 50% of the ceramic fibers are less than or equal to the L50 length value and 50% of the ceramic fibers are greater than the L50 length value (this is also known as the median length) and L90 can denote that 90% of the ceramic fibers are less than or equal to the L90 length value.

In some embodiments, the length of fifty percent of the ceramic fibers (i.e., the "L50"), based on a total number of the ceramic fibers, is at least 10 micrometers and the length of ninety percent (%) of the ceramic fibers (i.e., the "L90"), based on the total number of the ceramic fibers, is no greater than 500 micrometers. The L90 values (length of ninety % of the ceramic fibers based on the total number of the ceramic fibers) can also include any one of the following values: 400 micrometers or less, 300 micrometers or less, 200 micrometers or less, or 100 micrometers or less; while the L50 values (length of fifty % of the ceramic fibers based on a total number of the ceramic fibers) can also include any one of the following values: 15 micrometers or more, 20 micrometers or more, 25 micrometers or more, 30 micrometers or more, 35 micrometers or more, or 40 micrometers or more, where combinations of ranges for the L90 and L50 values are possible.

The ceramic fibers of the present disclosure can also have an arithmetic mean length. For example, the ceramic fibers of the composite material can an arithmetic mean length of 50 micrometers to less than 500 micrometers. Preferably, the ceramic fibers of the composite material can an arithmetic mean length of 50 micrometers to 250 micrometers.

The size and shape of the ceramic fibers of the composite material can further be described based on their aspect ratio (e.g., length-to-diameter ratio). It is appreciated that the cross-sectional shape of the ceramic fiber may not be exactly circular. As such, the cross-sectional area of the ceramic fiber can be used to arrive at a "diameter" value to be used for the aspect ratio discussed herein. For the present disclosure an aspect ratio of an arithmetic mean length of the ceramic fibers to an arithmetic mean diameter of the ceramic fibers is at least 5:1 (mean length:mean diameter), at least 10:1, at least 15:1, at least 20:1, at least 25:1, at least 30:1, at least 40:1, at least 50:1, at least 65:1, at least 75:1, at least 90:1, at least 100:1, at least 125:1, or at least 150:1; and 200:1 or less (mean length:mean diameter), 180:1 or less, 160:1 or less, 140:1 or less, 120:1 or less, 100:1 or less, 80:1 or less, or 60:1 or less.

Without wishing to be bound by theory, it is hypothesized that the use of ceramic fibers having diameters in the range of 0.3 to 5 micrometers provides two advantages. First, the small diameter of the fibers means that the length to diameter ratio (L/D) can be high, even for fibers chopped to short length. For instance, a 1 micrometer diameter fiber that is 100 micrometers long has an L/D of 100:1, whereas a 10 micrometer diameter fiber of the same length would only have an L/D of 10. In dental restoratives, short length is important since the size of the composites is small (a few millimeters or less). Small diameter fibers enable long L/D ratios even in very small samples. Secondly, in diametral tensile strength (DTS) testing, fibers are aligned transverse to the loading direction because DTS test discs are cut from a long tube into which the fiber-containing resin is extruded. The extrusion process aligns the fibers parallel to the tube axis, which is transverse to the DTS test loading direction. FIG. 1, for instance, is an SEM micrograph of a DTS fracture surface of a hardened composite material (of Example 4) containing MICROSTRAND 110X fibers 12 having a measured mean diameter of 2.05 micrometers. FIG. 1 shows that the hardened matrix material 12 contains a high degree of alignment of the fibers 14 perpendicular to the fracture surface.

Figure 2:
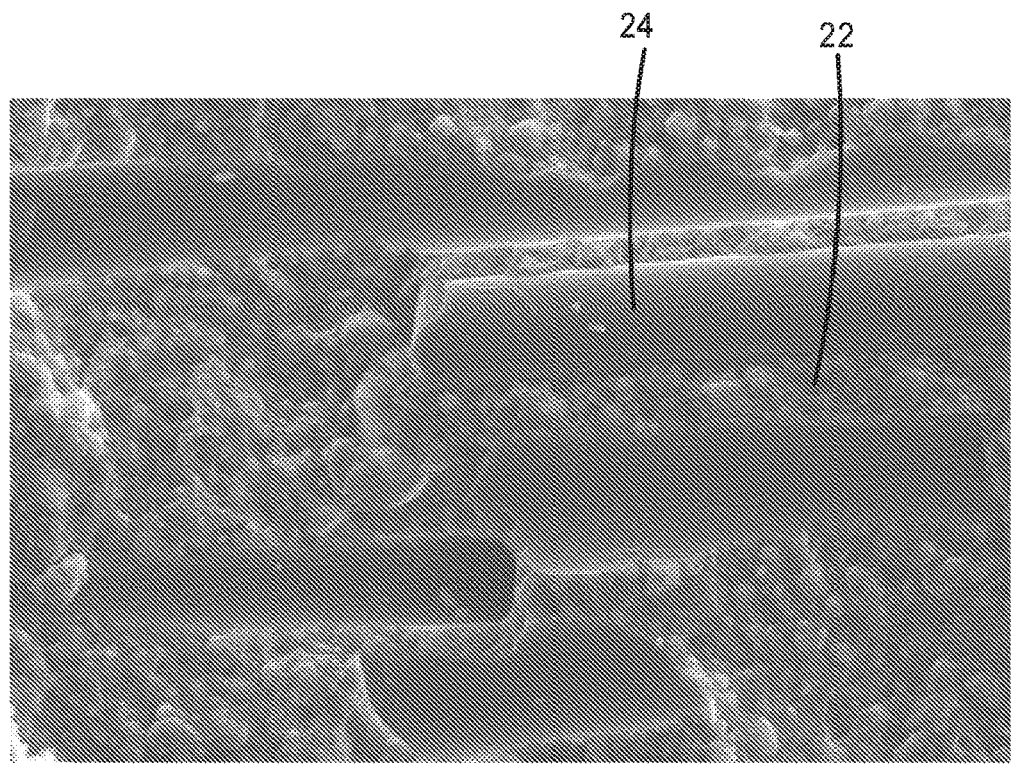
FIG. 2 is an SEM micrograph of a DTS fracture surface of a comparative hardened composite material.
Figure 3:
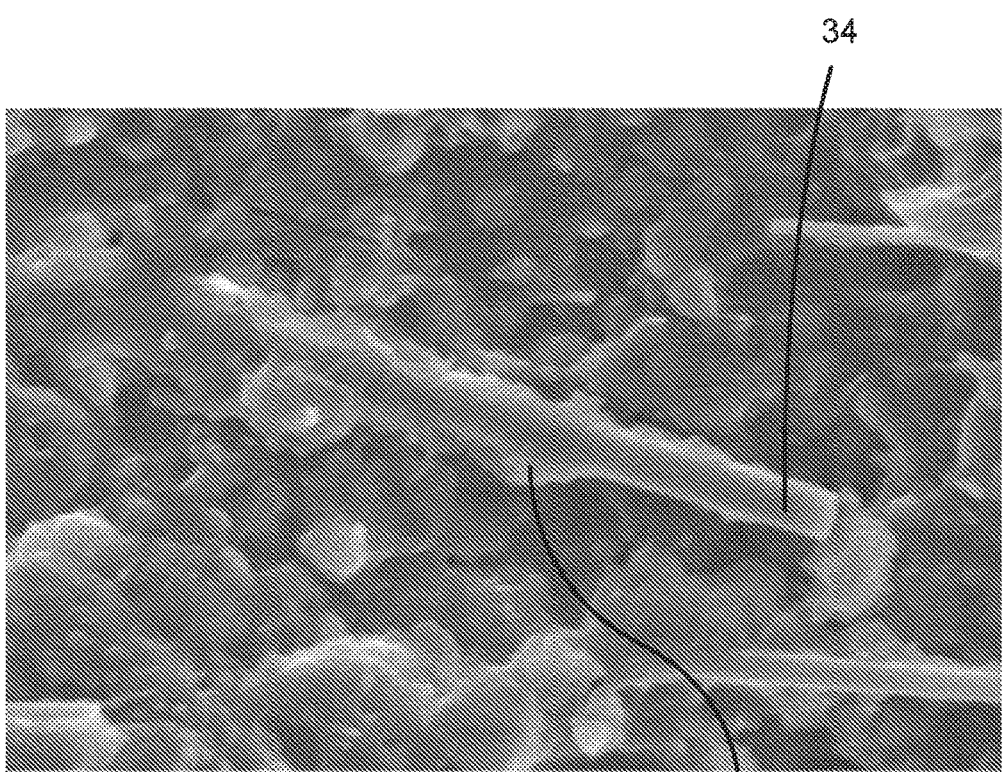
FIG. 3 is an SEM micrograph of a DTS fracture surface of another hardened composite material according to the present disclosure.

FIG. 2 is a (higher-resolution) SEM micrograph of a hardened composite material (of Comparative Example B) containing fibers having a 50/50 mixture of alumina and silica, having a reported diameter of about 15 micrometers. FIG. 2 shows that the fiber surfaces 24 are very clean, i.e., do not have residual matrix material 22 bonded to them. This suggests that fiber-matrix bonding is very weak. Thus, the ceramic fibers do not act as strength-increasing reinforcements in a DTS test, but are more accurately described as brittle, strength-limiting inclusions. In at least certain embodiments according to the present disclosure, small diameter fibers provide good fiber-matrix bonding. FIG. 3 shows a DTS fracture surface of a hardened composite material (of Example 3), containing MICROSTRAND 106 borosilicate glass fibers having a measured mean diameter of 0.35 micrometers. The matrix material 32 is shown in FIG. 3 to be bonded to much of the fiber surface 34, and strong fiber-matrix bonding contributes to high transverse strength in fiber-reinforced composites. DTS tests measured the strength of the composite transverse to the major fiber orientation. The smaller the fiber diameter, the smaller the strength limiting inclusion. In other words, the transverse loads in DTS testing can be distributed around smaller fibers more easily.

The ceramic fibers of the present disclosure can have a variety of compositions. Preferably, the ceramic fibers of the present disclosure are at least partially amorphous ceramic fibers or completely amorphous ceramic fibers. The ceramic fibers can be produced in continuous lengths, which are chopped or sheared, as discussed herein, to provide the ceramic fibers of the present disclosure.

In some embodiments, the ceramic fibers comprise alumina fibers, alumina-silica fibers, aluminum borosilicate fibers, zirconia-silica fibers, borosilicate glass fibers, silicate fibers modified with alkalis or alkaline earths, fused silica fibers, leached silica fibers, quartz fibers, fiberglass, or combinations thereof. In select embodiments, preferred ceramic fibers are composed of alumina-silica fibers, borosilicate glass fibers, or combinations thereof.

The ceramic fibers of the present disclosure can be produced from a variety of commercially available ceramic filaments. Examples of filaments useful in forming the ceramic fibers of the present disclosure include the alumina-silica fibers sold under the trade designations "FIBERFRAX CERAMIC FIBER BULK 7000" from Unifrax LLC (Niagara Falls, N.Y.), "SAFFIL LDM" and "SAFFIL 3D+ FIBER" from Cole-Parmer (Vernon Hills, Ill.). Another suitable alumina-silica fiber is similar to Example 1 of U.S. Pat. No. 4,047,965 (Karst, et al.). Ceramic fibers according to the present disclosure can also be formed from other suitable ceramic filaments, including glass fibers sold under the trade designations "JM MICRO-STRAND 106-475" and "JM MICRO-STRAND 110X-481" available from Johns Manville (Waterville, Ohio).

As discussed herein, the ceramic fibers of the present disclosure can be cut or chopped so as to provide the percentage of fibers lengths in the ranges discussed herein. Producing ceramic fibers having this range of lengths can be accomplished by cutting continuous filaments of the ceramic material in a mechanical shearing operation or laser cutting operation, among other cutting operations.

The composite material can include 6 to 40 wt. % of ceramic fibers based on the total weight of the composite material. For example, the composite material can include 6 wt. % or more, 7 wt. % or more, 8 wt. % or more, 9 wt. % or more, 10 wt. % or more, 12 wt. % or more, 14 wt. % or more, 16 wt. % or more, 18 wt. % or more; and 40 wt. % or less, 37 wt. % or less, 35 wt. % or less, 32 wt. % or less, 27 wt. % or less, 25 wt. % or less, 22 wt. % or less, or 20 wt. % or less of ceramic fibers based on the total weight of the composite material. Stated another way, the composite material can contain 6 to 40 wt. %, 6 to 30 wt. %, or 10 to 20 wt. % of the ceramic fibers, based on the total weight of the composite material. As discussed herein, for a given combination of components that forms the composite material the wt. % of each of the components adds to 100 wt. % (wt. % based on the total weight of the composite material).

Some suitable ceramic fibers are commercially available pre-treated with organic sizings or finishes which serves as aids in textile processing. Sizing can include the use of starch, oil, wax or other organic ingredients applied to the filament strand to protect and aid handling. Sizings can also include a surface treatment, such as with a silane, where the surface treatment may or may not include polymerizable groups. The sizing can be removed from the ceramic filaments by heat treating the filaments or ceramic fibers as a temperature of 700° C. for one to four hours.

One or more (e.g., two or more) of a coupling agent can also be used with the ceramic fibers, either as received or after they have been treated to remove any sizing and/or to increase their surface area. One or more of the coupling agent can also be used with the filler particles, as discussed herein. So, combinations of two or more coupling agents, as discussed herein, can be used with the ceramic fiber and filler particles, when present, in the composite material. In some embodiments, such coupling agents can help to provide a chemical bond (e.g., a covalent bond) between the polymerizable component and the ceramic fibers and, when present, the filler particles. The coupling agent is a compound capable of reacting with both the polymerizable component and the ceramic fibers and the filler particles (when present), thereby acting as an interface between the polymerized polymerizable component and the ceramic fibers and the filler particles (when present). The ceramic fibers and the filler particles (when present) can be treated with the coupling agent prior to admixing with the polymerizable component. Thus, in some embodiments, the coupling agent includes a polymerizable group, such as for example one or more epoxy, acrylate and/or (meth)acrylate groups. In other embodiments, the coupling agent does not include a polymerizable group.

In some embodiments, the coupling agent can be selected from the group consisting of an organosilane coupling agent, a titanate coupling agent, a zirconate coupling agent, an acidic coupling agent or a combination thereof. The coupling agent may be applied to the inorganic materials (e.g., the ceramic fibers and filler particles, when present) as a pre-treatment and/or added to the polymerizable component.

Organosilane coupling agents have the general formula $R_nSiX_{(4-n)}$. The functional group "X" is involved in the reaction with the substrate, where X is independently at each occurrence a hydrolyzable group such as an alkoxy, an acyloxy or an amine. R is a non-hydrolyzable organic radical that possesses a functionality that enables the organosilane coupling agent to bond with, or improve compatibility with, organic polymers and the like. Suitable examples of organosilane coupling agents include gamma-methacryloxypropyltrimethoxysilane, gamma-methacryloxyoctyltrimethoxysilane, gamma-mercaptopropyltriethoxysilane, gamma-aminopropyltrimethoxysilane, beta-(3,4-epoxycyclohexyl)ethyltrimethoxysilane, gamma-glycidoxypropyltrimethoxysilane, and the like. Other suitable examples of organosilane coupling agents include n-octyltrimethoxysilane, phenyltrimethoxysilane, and the like. Mixtures of organosilane coupling agents may be used.

Titanate coupling agents include a family of monoalkoxy titanates useful in conjunction with the ceramic fibers and the filler particles, when present. Titanate couplers typically have three pendant organic functional groups. The titanate couplers also act as plasticizers to enable much higher loadings and/or to achieve better flow. A suitable example of a titanate coupling reagent includes methoxydiethyleneglycol trimethacryloyl titanate.

Zirconate coupling agents include 2,2-di(allyloxymethyl) butyl trimethacryloyl zirconate.

Acidic coupling agents include mono-2-(methacryloyloxy)ethyl succinate.

The composite material of the present disclosure is hardenable due the presence of the polymerizable component. The composite material typically includes 20 to 40 wt. % of the polymerizable component. In some embodiments, the composite material can be hardened (e.g., polymerized by conventional photopolymerization and/or chemical polymerization techniques) prior to applying it to an oral surface. In other embodiments, the composite material can be hardened (e.g., polymerized by conventional photopolymerization and/or chemical polymerization techniques) after it has been applied to an oral surface.

Examples of the polymerizable component include, but are not limited to, those having sufficient strength, hydrolytic stability, and non-toxicity to render them suitable for use in the oral environment. Examples of such materials include acrylates, methacrylates, urethanes, carbamoylisocyanurates and epoxy resins (e.g., those shown in U.S. Pat. No. 3,066,112 (Bowen); U.S. Pat. No. 3,539,533 (Lee I I, et al.); U.S. Pat. No. 3,629,187 (Waller); U.S. Pat. No. 3,709,866 (Waller); U.S. Pat. No. 3,751,399 (Lee, et al.); U.S. Pat. No. 3,766,132 (Lee, et al.); U.S. Pat. No. 3,860,556 (Taylor); U.S. Pat. No. 4,002,669 (Gross, et al.); U.S. Pat. No. 4,115,346 (Gross, et al.); U.S. Pat. No. 4,259,117 (Yamauchi, et al.); U.S. Pat. No. 4,292,029 (Craig, et al.); U.S. Pat. No. 4,308,190 (Walkowiak, et al.); U.S. Pat. No. 4,327,014 (Kawahara, et al.); U.S. Pat. No. 4,379,695 (Orlowski, et al.); U.S. Pat. No. 4,387,240 (Berg); U.S. Pat. No. 4,404,150 (Tsunekawa, et al.)); and mixtures and derivatives thereof.

In certain embodiments, the polymerizable component of the composite material is photopolymerizable, i.e., the polymerizable component contains a photoinitiator system that upon irradiation with actinic radiation initiates the polymerization (or hardening) of the composite material. In other embodiments, the polymerizable component of the composite material is chemically hardenable, i.e., the polymerizable component contains a chemical initiator (i.e., initiator system) that can polymerize, cure, or otherwise harden the composite material without dependence on irradiation with actinic radiation. Such chemically hardenable compositions are sometimes referred to as "self-cure" compositions.

The polymerizable component typically includes one or more ethylenically unsaturated compounds with or without acid functionality. Examples of useful ethylenically unsaturated compounds include acrylic acid esters, methacrylic acid esters, hydroxy-functional acrylic acid esters, hydroxy-functional methacrylic acid esters, and combinations thereof.

The composite material, especially in photopolymerizable implementations, may include compounds having free radically active functional groups that may include monomers, oligomers, and polymers having one or more ethylenically unsaturated group. Suitable compounds contain at least one ethylenically unsaturated bond and are capable of undergoing addition polymerization. Such free radically polymerizable compounds include mono-, di- or poly-(meth)acrylates (i.e., acrylates and methacrylates) such as, methyl (meth)acrylate, ethyl acrylate, isopropyl methacrylate, n-hexyl acrylate, stearyl acrylate, allyl acrylate, glycerol triacrylate, ethyleneglycol diacrylate, diethyleneglycol diacrylate, triethyleneglycol dimethacrylate, 1,3-propanediol di(meth)acrylate, trimethylolpropane triacrylate, 1,2,4-butanetriol trimethacrylate, 1,4-cyclohexanediol diacrylate, pentaerythritol tetra(meth)acrylate, sorbitol hexacrylate, tetrahydrofurfuryl (meth)acrylate, bis[1-(2-acryloxy)]-p-ethoxyphenyldimethylmethane, bis[1-(3-acryloxy-2-hydroxy)]-p-propoxyphenyldimethylmethane, ethoxylated bisphenol A di(meth)acrylate, and trishydroxyethyl-isocyanurate trimethacrylate; (meth)acrylamides (i.e., acrylamides and methacrylamides) such as (meth)acrylamide, methylene bis-(meth)acrylamide, and diacetone (meth)acrylamide; urethane (meth)acrylates; the bis-(meth)acrylates of polyethylene glycols (preferably of molecular weight 200-500), copolymerizable mixtures of acrylated monomers such as those in U.S. Pat. No. 4,652,274 (Boettcher et al.), acrylated oligomers such as those of U.S. Pat. No. 4,642,126 (Zador et al.), and poly(ethylenically unsaturated) carbamoyl isocyanurates such as those disclosed in U.S. Pat. No. 4,648,843 (Mitra); and vinyl compounds such as styrene, diallyl phthalate, divinyl succinate, divinyl adipate and divinyl phthalate. Other suitable free radically polymerizable compounds include siloxane-functional (meth)acrylates as disclosed, for example, in WO-00/38619 (Guggenberger et al.), WO-01/92271 (Weinmann et al.), WO-01/07444 (Guggenberger et al.), WO-00/42092 (Guggenberger et al.) and fluoropolymer-functional (meth)acrylates as disclosed, for example, in U.S. Pat. No. 5,076,844 (Fock et al.), U.S. Pat. No. 4,356,296 (Griffith et al.), EP-0373 384 (Wagenknecht et al.), EP-0201 031 (Reiners et al.), and EP-0201 778 (Reiners et al.). Mixtures of two or more free radically polymerizable compounds can be used if desired. In some embodiments, a methacryloyl-containing compound may be utilized.

The polymerizable component may also contain hydroxyl groups and ethylenically unsaturated groups in a single molecule. Examples of such materials include hydroxyalkyl (meth)acrylates, such as 2-hydroxyethyl (meth)acrylate and 2-hydroxypropyl (meth)acrylate; glycerol mono- or di-(meth)acrylate; trimethylolpropane mono- or di-(meth)acrylate; pentaerythritol mono-, di-, and tri-(meth)acrylate; sorbitol mono-, di-, tri-, tetra-, or penta-(meth)acrylate; and 2,2-bis[4-(2-hydroxy-3-methacryloxypropoxy)phenyl]propane (bisGMA). Suitable ethylenically unsaturated compounds are also available from a wide variety of commercial sources, such as Sigma-Aldrich, St. Louis. Mixtures of ethylenically unsaturated compounds can be used if desired.

In certain embodiments, the polymerizable component includes a compound selected from the group consisting of dimethacrylates of polyethylene glycols of 200 to 1000 weight average molecular weight, such as PEGDMA (polyethyleneglycol dimethacrylate having a molecular weight of approximately 400), UDMA (urethane dimethacrylate), GDMA (glycerol dimethacrylate), TEGDMA (triethyleneglycol dimethacrylate), 2 to 10 mole ethoxylated Bisphenol-A dimethacrylate (Bis-EMA), such as bisEMA6 as described in U.S. Pat. No. 6,030,606 (Holmes), NPGDMA (neopentylglycol dimethacrylate), glycerol dimethacrylate, 1,3-propanediol dimethacrylate and 2-hydroxethyl methacrylate. Various combinations of these hardenable components can be used. For certain embodiments, including any one of the above embodiments, the polymerizable resin comprises a compound selected from the group consisting of 2,2-bis[4-(2-hydroxy-3-methacryloyloxypropoxy)phenyl]propane (bisGMA), triethyleneglycol dimethacrylate (TEGDMA), urethane dimethacrylate (UDMA), 2 to 10 mole ethoxylated Bisphenol-A dimethacrylate (bisEMA), dimethacrylates of polyethylene glycols of 200 to 1000 weight average molecular weight, glycerol dimethacrylate, 1,3-propanediol dimethacrylate, and a combination thereof.

When the composite material contains an ethylenically unsaturated compound without acid functionality, it is generally present in an amount of at least 5% by weight, more typically at least 10% by weight, and most typically at least 15% by weight ethylenically unsaturated compounds without acid functionality, based on the total weight of the unfilled composition. The compositions of the present disclosure typically include at most 95% by weight, more typically at most 90% by weight, and most typically at most 80% by weight ethylenically unsaturated compounds without acid functionality, based on the total weight of the unfilled composition.

In some embodiments, the polymerizable component may include one or more ethylenically unsaturated compounds with acid functionality. As used herein, ethylenically unsaturated compounds "with acid functionality" is meant to include monomers, oligomers, and polymers having ethylenic unsaturation and acid and/or acid-precursor functionality. Acid-precursor functionalities include, for example, anhydrides, acid halides, and pyrophosphates. The acid functionality can include carboxylic acid functionality, phosphoric acid functionality, phosphonic acid functionality, sulfonic acid functionality, or combinations thereof.

Ethylenically unsaturated compounds with acid functionality include, for example, α, β-unsaturated acidic compounds such as glycerol phosphate mono(meth)acrylates, glycerol phosphate di(meth)acrylates, hydroxyethyl (meth)acrylate (e.g., HEMA) phosphates, bis((meth)acryloxyethyl) phosphate, ((meth)acryloxypropyl) phosphate, bis((meth)acryloxypropyl) phosphate, bis((meth)acryloxy)propyloxy phosphate, (meth)acryloxyhexyl phosphate, bis((meth)acryloxyhexyl) phosphate, (meth)acryloxyoctyl phosphate, bis ((meth)acryloxyoctyl) phosphate, (meth)acryloxydecyl phosphate, bis((meth)acryloxydecyl) phosphate, caprolactone methacrylate phosphate, citric acid di- or tri-methacrylates, poly(meth)acrylated oligomaleic acid, poly(meth) acrylated polymaleic acid, poly(meth)acrylated poly(meth)acrylic acid, poly(meth)acrylated polycarboxyl-polyphosphonic acid, poly(meth)acrylated polychlorophosphoric acid, poly(meth)acrylated polysulfonate, poly(meth)acrylated polyboric acid, and the like, may be used as components in the hardenable component system. Also monomers, oligomers, and polymers of unsaturated carbonic acids such as (meth)acrylic acids, aromatic (meth)acrylated acids (e.g., methacrylated trimellitic acids), and anhydrides thereof can be used. Certain preferred compositions of the present disclosure include an ethylenically unsaturated compound with acid functionality having at least one P—OH moiety.

When the composition contains an ethylenically unsaturated compound with acid functionality, it is generally present in an amount of at least 1% by weight, more typically at least 3% by weight, and most typically at least 5% by weight ethylenically unsaturated compounds with acid functionality, based on the total weight of the unfilled composition. The compositions of the present disclosure typically include at most 80% by weight, more typically at most 70% by weight, and most typically at most 60% by weight ethylenically unsaturated compounds with acid functionality, based on the total weight of the unfilled composition.

For free radical polymerization (hardening), an initiation system can be selected from systems which initiate polymerization via radiation, heat, or redox/auto-cure chemical reaction. A class of initiators capable of initiating polymerization of free radically active functional groups includes free radical-generating photoinitiators, optionally combined with a photosensitizer or accelerator. Such initiators typically can be capable of generating free radicals for addition polymerization upon exposure to light energy having a wavelength between 200 and 800 nm.

In certain embodiments, one or more thermally activated initiators are used to enable thermal hardening of the polymerizable component. Examples of thermal initiators include peroxides and azo compounds such as benzoyl peroxide, lauryl peroxide, 2,2-azobis-isobutyronitrile (AIBN).

In certain embodiments, the thermally activated initiator is chosen such that appreciable amounts of free-radical initiating species are not produced at temperatures below about 100° C. "Appreciable amounts" refers an amount sufficient to cause polymerization and/or crosslinking to the extent that a noticeable change in properties (e.g., viscosity, moldability, hardness, etc.) of the composite material occurs. For certain embodiments, the initiator is activated within the temperature range of 120 to 140° C., or, in some embodiments, 130 to 135° C. For certain of these embodiments, the initiator is an organic peroxide which can be thermally activated to produce appreciable amounts of free-radical initiating species within any of these temperature ranges. For certain of these embodiments, the initiator is selected from the group consisting of dicumyl peroxide, t-butyl peroxide, and a combination thereof. For certain of these embodiments, the initiator is dicumyl peroxide. In other embodiments, the initiator is selected from 2,5-bis(tert-butylperoxy)-2,5-dimethylhexane; 2,5-bis(tert-butylperoxy)-2,5-dimethyl-3-hexyne; bis(1-(tert-butylperoxy)-1-methylethyl)benzene; tert-butyl peracetate; tert-butyl peroxybenzoate; cumene hydroperoxide; 2,4-pentanedione peroxide; peracetic acid, and combinations thereof.

For certain embodiments, the thermally activated initiator is present in the composition in an amount of at least 0.2 percent based upon the weight of the polymerizable component. For certain of these embodiments, the initiator is present in an amount of at least 0.5 percent. For certain of these embodiments, the initiator is present in the composition in the amount of not more than 3 percent based upon the weight of the polymerizable component. For certain of these embodiments, the initiator is present in an amount of not more than 2 percent.

In certain embodiments, the composition may additionally be photopolymerizable, i.e., the composition contains a photoinitiator system that upon irradiation with actinic radiation initiates polymerization (curing or hardening) of the composition. Suitable photoinitiators (i.e., photoinitiator systems that include one or more compounds) for polymerizing free radically photopolymerizable components include binary and tertiary systems. Typical tertiary photoinitiators include an iodonium salt, a photosensitizer, and an electron donor compound as described in U.S. Pat. No. 5,545,676 (Palazzotto et al.). Suitable iodonium salts are the diaryl iodonium salts, e.g., diphenyliodonium chloride, diphenyliodonium hexafluorophosphate, diphenyliodonium tetrafluoroborate, and tolylcumyliodonium tetrakis(pentafluorophenyl)borate. Suitable photosensitizers are monoketones and diketones that absorb some light within a range of 400 nm to 520 nm (preferably, 450 nm to 500 nm). Particularly suitable compounds include alpha diketones that have light absorption within a range of 400 nm to 520 nm (even more preferably, 450 to 500 nm). Suitable compounds are camphorquinone, benzil, furil, 3,3,6,6-tetramethylcyclohexanedione, phenanthraquinone, 1-phenyl-1,2-propanedione and other 1-aryl-2-alkyl-1,2-ethanediones, and cyclic alpha diketones. Suitable electron donor compounds include substituted amines, e.g., ethyl dimethylaminobenzoate. Other suitable tertiary photoinitiator systems useful for photopolymerizing cationically polymerizable resins are described, for example, in U.S. Pat. No. 6,765,036 (Dede et al.).

Other useful photoinitiators for polymerizing free radically photopolymerizable components include the class of phosphine oxides that typically have a functional wavelength range of 380 nm to 1200 nm. Preferred phosphine oxide free radical initiators with a functional wavelength range of 380 nm to 450 nm are acyl and bisacyl phosphine oxides such as those described in U.S. Pat. No. 4,298,738 (Lechtken et al.), U.S. Pat. No. 4,324,744 (Lechtken et al.), U.S. Pat. No. 4,385,109 (Lechtken et al.), U.S. Pat. No. 4,710,523 (Lechtken et al.), and U.S. Pat. No. 4,737,593 (Ellrich et al.), U.S. Pat. No. 6,251,963 (Kohler et al.); and EP Application No. 0 173 567 A2 (Ying).

Commercially available phosphine oxide photoinitiators capable of free-radical initiation when irradiated at wavelength ranges of different from 380 nm to 450 nm include bis(2,4,6-trimethylbenzoyl)phenyl phosphine oxide (OMNIRAD 819, IGM Resins (Waalwijk, The Netherlands)), bis (2,6-dimethoxybenzoyl)-(2,4,4-trimethylpentyl) phosphine oxide (CGI 403, Ciba Specialty Chemicals), a 1:1 mixture, by weight, of bis(2,4,6-trimethylbenzoyl)phenyl phosphine oxide and 2-hydroxy-2-methyl-1-phenylpropane-1-one (DAROCUR 4265, Ciba Specialty Chemicals), and ethyl 2,4,6-trimethylbenzylphenyl phosphinate (LUCIRIN LR8893X, BASF Corp., Charlotte, N.C.).

The phosphine oxide initiator may be used in the composite material in catalytically effective amounts, such as from 0.1 weight percent to 5.0 weight percent, based on the total weight of the unfilled composition.

Tertiary amine reducing agents may be used in combination with an acylphosphine oxide. Illustrative tertiary amines useful in the disclosure include ethyl 4-(N,N-dimethylamino)benzoate and N,N-dimethylaminoethyl methacrylate. When present, the amine reducing agent is present in the composite material in an amount from 0.1 weight percent to 5.0 weight percent, based on the total weight of the unfilled composition. Useful amounts of other initiators are well known to those of skill in the art.

Polymerizable components made from cationically curable material suitable for use in the present disclosure can also include epoxy resins. Epoxy resins impart high toughness to composites, a desirable feature, for example, dental mill blanks. Epoxy resins may optionally be blended with various combinations of polyols, methacrylates, acrylates, or vinyl ethers. Preferred epoxy resins include diglycidyl ether of bisphenol A (e.g., EPON 828, EPON 825; Shell Chemical Co.), 3,4-epoxycyclohexylmethyl-3-4-epoxy cyclohexene carboxylate (e.g., UVR-6105, Union Carbide), bisphenol F epoxides (e.g., GY-281; Ciba-Geigy), and polytetrahydrofuran.

As used herein, "cationically active functional groups" is a chemical moiety that is activated in the presence of an initiator capable of initiating cationic polymerization such that it is available for reaction with other compounds bearing cationically active functional groups. Materials having cationically active functional groups include cationically polymerizable epoxy resins. Such materials are organic compounds having an oxirane ring, i.e., a group which is polymerizable by ring opening. These materials include monomeric epoxy compounds and epoxides of the polymeric type and can be aliphatic, cycloaliphatic, aromatic or heterocyclic. These materials generally have, on the average, at least 1 polymerizable epoxy group per molecule, preferably at least about 1.5 and more preferably at least about 2 polymerizable epoxy groups per molecule. The polymeric epoxides include linear polymers having terminal epoxy groups (e.g., a diglycidyl ether of a polyoxyalkylene glycol), polymers having skeletal oxirane units (e.g., polybutadiene polyepoxide), and polymers having pendent epoxy groups (e.g., a glycidyl methacrylate polymer or copolymer). The epoxides may be pure compounds or may be mixtures of compounds containing one, two, or more epoxy groups per molecule. The "average" number of epoxy groups per molecule is determined by dividing the total number of epoxy groups in the epoxy-containing material by the total number of epoxy-containing molecules present.

These epoxy-containing materials may vary from low molecular weight monomeric materials to high molecular weight polymers and may vary greatly in the nature of their backbone and substituent groups. Illustrative of permissible substituent groups include halogens, ester groups, ethers, sulfonate groups, siloxane groups, nitro groups, phosphate groups, and the like. The weight average molecular weight of the epoxy-containing materials may vary from about 58 to about 100,000 or more. Molecular weights (e.g., weight average molecular weights) for the present disclosure are measured using size exclusion chromatography with polystyrene standards.

Useful epoxy-containing materials include those which contain cyclohexane oxide groups such as epoxycyclohexanecarboxylates, typified by 3,4-epoxycyclohexylmethyl-3,4-epoxycyclohexanecarboxylate, 3,4-epoxy-2-methylcyclohexylmethyl-3,4-epoxy-2-methylcyclohexane carboxylate, and bis(3,4-epoxy-6-methylcyclohexylmethyl) adipate. For a more detailed list of useful epoxides of this nature, reference is made to U.S. Pat. No. 3,117,099 (Proops, et al.), which is incorporated herein by reference.

Blends of various epoxy-containing materials are also contemplated. Examples of such blends include two or more weight average molecular weight distributions of epoxy-containing compounds, such as low molecular weight (below 200), intermediate molecular weight (about 200 to 10,000) and higher molecular weight (above about 10,000). Alternatively or additionally, the epoxy resin may contain a blend of epoxy-containing materials having different chemical natures, such as aliphatic and aromatic, or functionalities, such as polar and non-polar. Other types of useful materials having cationically active functional groups include vinyl ethers, oxetanes, spiro-orthocarbonates, spiro-orthoesters, and the like.

For hardening polymerizable components comprising cationically active functional groups, an initiation system can be selected from systems which initiate polymerization via radiation, heat, or redox/auto-cure chemical reaction. For example, epoxy polymerization may be accomplished by the use of thermal curing agents, such as anhydrides or amines. A particularly useful example of an anhydride curing agent would be cis-1,2-cyclohexanedicarboxylic anhydride.

Alternatively, initiation systems for polymerizable components comprising cationically active functional groups are those that are photoactivated. The broad class of cationic photoactive groups recognized in the catalyst and photoinitiator industries may be used in the practice of the present disclosure. Photoactive cationic nuclei, photoactive cationic moieties, and photoactive cationic organic compounds are art recognized classes of materials as exemplified by U.S. Pat. No. 4,250,311 (Crivello); U.S. Pat. No. 3,708,296 (Schlesinger); U.S. Pat. No. 4,069,055 (Crivello); U.S. Pat. No. 4,216,288 (Crivello); U.S. Pat. No. 5,084,586 (Farooq); U.S. Pat. No. 5,124,417 (Farooq); U.S. Pat. No. 4,985,340 (Palazzotto, et al.), U.S. Pat. No. 5,089,536 (Palazzotto), and U.S. Pat. No. 5,856,373 (Kaisaki, et al.), each of which is incorporated herein by reference.

The cationically-curable materials can be combined with a three component or ternary photoinitiator system, as described above. Three component initiator systems are also described in U.S. Pat. No. 6,025,406 (Oxman, et al.) and U.S. Pat. No. 5,998,549 (Milbourn, et al.), each of which is incorporated herein by reference.

The chemically hardenable compositions may include redox cure systems that include a polymerizable component (e.g., an ethylenically unsaturated polymerizable component) and redox agents that include an oxidizing agent and a reducing agent. The reducing and oxidizing agents should react with or otherwise cooperate with one another to produce free-radicals capable of initiating polymerization of the polymerizable component (e.g., the ethylenically unsaturated component). This type of cure is a dark reaction, that is, it is not dependent on the presence of light and can proceed in the absence of light. The reducing and oxidizing agents are preferably sufficiently shelf-stable and free of undesirable colorization to permit their storage and use under typical dental conditions.

Useful reducing agents include ascorbic acid, ascorbic acid derivatives, and metal complexed ascorbic acid compounds; amines, especially tertiary amines, such as 4-tert-butyl dimethylaniline; aromatic sulfinic salts, such as p-toluenesulfinic salts and benzenesulfinic salts; thioureas, such as 1-ethyl-2-thiourea, tetraethyl thiourea, tetramethyl thiourea, 1,1-dibutyl thiourea, and 1,3-dibutyl thiourea; and mixtures thereof. Other secondary reducing agents may include cobalt (II) chloride, ferrous chloride, ferrous sulfate, hydrazine, hydroxylamine (depending on the choice of oxidizing agent), salts of a dithionite or sulfite anion, and mixtures thereof. Preferably, the reducing agent is an amine.

Suitable oxidizing agents will also be familiar to those skilled in the art, and include but are not limited to persulfuric acid and salts thereof, such as sodium, potassium, ammonium, cesium, and alkyl ammonium salts. Additional oxidizing agents include peroxides such as benzoyl peroxides, hydroperoxides such as cumyl hydroperoxide, t-butyl hydroperoxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and mixtures thereof.

It may be desirable to use more than one oxidizing agent or more than one reducing agent. Small quantities of transition metal compounds may also be added to accelerate the rate of redox cure.

The reducing and oxidizing agents are present in amounts sufficient to permit an adequate free-radical reaction rate. This can be evaluated by combining all of the ingredients of the composition except for the optional filler, and observing whether or not a hardened mass is obtained.

Typically, the reducing agent, if used at all, is present in an amount of at least 0.01% by weight, and more typically at least 0.1% by weight, based on the total weight of the components of the unfilled composition. Typically, the reducing agent is present in an amount of no greater than 10% by weight, and more typically no greater than 5% by weight, based on the total weight of the components of the unfilled composition.

Typically, the oxidizing agent, if used at all, is present in an amount of at least 0.01% by weight, and more typically at least 0.10% by weight, based on the total weight of the components of the unfilled composition. Typically, the oxidizing agent is present in an amount of no greater than 10% by weight, and more typically no greater than 5% by weight, based on the total weight of the components of the unfilled composition.

When used as a dental restorative material, the composite material can have a variety of weight percent values for the ceramic fibers and/or the nanoclusters depending upon the dental application. So, for example, if used as a sealant, the composite material of the disclosure can be filled with the ceramic fibers and/or the nanoclusters so as to provide a flowable composite. In such implementations, the viscosity of the composite material is sufficiently low to allow its penetration into pits and fissures of occlusal tooth surfaces as well as into etched areas of enamel, thereby aiding in the retention of the composite material. In applications where high strength or durability are desired (e.g., anterior or posterior restoratives, prostheses, crown and bridge cements, artificial crowns, artificial teeth and dentures) the loading level of the ceramic fibers and the nanoclusters can be tailored so as to provide a more rigid composite.

The composite material further includes 30 to 70 wt. % of nanoclusters. The composite material can also include other value ranges for the nanoclusters. For example, the composite material can also include for the wt. % of the nanoclusters lower limit values of: 30, 35, 40, or 45, and upper limit values of 70, 65, 64, 60, 55, or 50. This allows for a variety of possible ranges for the wt. % of the nanoclusters in the composite material. Examples of such ranges include, but are not limited to, 30 to 70 wt. % of nanoclusters, 35 to 65 wt. % of nanoclusters, 30 to 60 wt. % of nanoclusters, 30 to 55 wt. % of nanoclusters, where a range of 35 to 64 wt. % of nanoclusters is preferred.

As discussed herein, for a given combination of components that forms the composite material the wt. % of each of the components adds to 100 wt. % (wt. % based on the total weight of the composite material). Preferably, the nanoclusters are silica-zirconia nanoclusters formed from silica nanoparticles and zirconia that associate by relatively weak intermolecular forces that cause the silica nanoparticles and zirconia to clump together, even when dispersed in the polymerizable component of the present disclosure. The silica nanoparticles and zirconia (the "primary particles" that form the silica-zirconia nanoclusters) can have a mean diameter of 1 nanometer (nm) to 200 nm, where the resulting silica-zirconia nanoclusters can have a longest dimension in the micrometer range (e.g., 10 micrometers) from the association or "nanocluster" of the silica nanoparticles and zirconia. The primary particles forming the silica-zirconia nanoclusters (e.g., the silica nanoparticles and zirconia) can be grouped together in an amorphous cluster formation. The cluster formation of the silica nanoparticles and zirconia, however, is not limited to such an amorphous cluster formation.

Silica-zirconia nanoclusters may be prepared by mixing a nanosilica sol together with a preformed nanozirconia particulate sol or a zirconium salt (e.g., an acetate or nitrate salt) solution. When a nanozirconia sol is used it is typically composed of crystalline zirconia nanoparticles. The nanosilica sol typically comprises silica particles having a mean diameter from 1 to 200 nm, more typically 10 nm to 100 nm, even more typically from 15 nm to 60 nm, most typically from 15 nm to 35 nm, with a mean particle diameter of about 20 nm being particularly well-suited for fabrication of the silica-zirconia nanoclusters.

The zirconia sol typically comprises zirconia particles that are small enough to not scatter the majority of visible light, but are large enough to refract shorter wavelength blue light to give the opalescent effect. A zirconia sol having a mean particle size from about 3 nm to about 30 nm is suitable for forming the silica-zirconia nanoclusters. Typically, the zirconia particles in the sol have a mean particle diameter from 5 nm to 15 nm, more typically from 6 nm to 12 nm, and most typically from 7 nm to 10 nm. When mixed together under acidic conditions where the sol mixture is stable, such as at a pH of below 2, the preformed zirconia nanoparticles form a structure with the silica nanoparticles on gelling and drying that gives the desired opalescence character while maintaining a high level of optical translucency of the final composite material.

NALCO 1042 silica sol (Ecolab, Inc., St. Paul, Minn.), NALCO 1034A, or other commercially available colloidal silica sols may be used. If a base-stabilized sol is used, typically it will first be subjected to ion exchange in order to remove sodium, for example, with an AMBERLITE IR-120 ion exchange resin, or pH adjusted with nitric acid. It is usually desirable to pH adjust the silica to below 1.2, typically about 0.8 to about 1.0, and then add the zirconia to it slowly, to prevent localized gelation and agglomeration. The pH of the resultant mixture is typically about 1.1 to about 1.2. Suitable colloidal silica sols are available from a variety of vendors, and include NALCO (Ecolab), sols from H. C. Stark, SNOWTEX (Nissan Chemical America Corporation Houston, Tex.), sols from Nyacol Nano Technologies, Inc. (Ashland, Mass.), and LUDOX (W.R. Grace & Company Columbia, Md.). The selected sol should have silica particles that are discrete and of the appropriate size specified herein. The silica sol may be treated to provide a highly acidic silica sol (e.g., nitrate stabilized) that can be mixed with the zirconia sol without gelation.

The zirconia sol may be obtained using a process described, for example, in U.S. Pat. No. 6,376,590 (Kolb, et al.), or U.S. Pat. No. 7,429,422 (Davidson et al.) the disclosures of which are incorporated by reference herein. As used herein, the term "zirconia" refers to various stoichiometries for zirconium oxides, most typically $ZrO_2$, and may also be known as zirconium oxide or zirconium dioxide. The zirconia may contain up to 30 weight percent of other chemical moieties such as, for example, $Y_2O_3$ and organic material.

The silica-zirconia nanoclusters can be prepared by mixing together the nanosilica sol with the nanozirconia sol, and heating the mixture to at least 450° C. Typically, the mixture is heated for 4 to 24 hours at a temperature between about 400 to about 1000° C., more typically from about 450 to about 950° C., to remove water, organic materials, and other volatile components, as well as to potentially weakly aggregate the particles (not required). Alternatively, or in addition, the sol mixture may undergo a different processing step to remove water and volatiles. The resulting material may be milled or ground and classified to remove large aggregates. The silica-zirconia nanoclusters may then be surface treated with, for example, a silane prior to mixing with a polymerizable component.

The composite material of the present disclosure can also include, optionally, one or more of filler particles in addition to the ceramic fibers. Such filler particles may be selected from one or more of a wide variety of materials suitable for incorporation in composite materials used for dental applications, such as filler particles currently used in dental restorative compositions, and the like. The choice of the filler particle can affect properties of the composite material such as its appearance, radiopacity and physical and mechanical properties. Appearance is affected in part by adjustment of the amounts and relative refractive indices of the ingredients of the composite, thereby allowing alteration of the translucence, opacity or pearlescence of the composite. In this way, the appearance of the composite material can, if desired, be made to closely approximate the appearance of natural dentition.

Filler particles may be selected from one or more of material suitable for incorporation in compositions used for medical applications, such as filler particles currently used in dental restorative compositions and the like. The maximum particle size (the largest dimension of a particle, generally, the diameter) of the filler particles is typically less than 20 micrometers, more typically less than 10 micrometers, and most typically less than 5 micrometers. The number average particle size diameter of the filler particles is typically no greater than 100 nm, and more typically no greater than 75 nm. The filler particles can have a unimodal or polymodal (e.g., bimodal) particle size distribution. The filler particles can be an inorganic material. It can also be a crosslinked organic material that is insoluble in the polymerizable component, and is optionally filled with inorganic filler. The filler particle should in any event be suitable for use in the mouth. The filler particle can be radiopaque, radiolucent or non-radiopaque. The filler particle typically is substantially insoluble in water. The filler particle may have a variety of shapes, including but not limited to equiaxed, spherical, polyhedral, oblong, lenticular, toroidal or whisker.

Examples of suitable filler particles are naturally-occurring or synthetic materials such as quartz, nitrides (e.g., silicon nitride); glasses containing, for example Ce, Sb, Sn, Sr, Ba, An, and Al; colloidal silica; feldspar; borosilicate glass; kaolin; talc; titania; and zinc glass; low Mohs hardness fillers such as those described in U.S. Pat. No. 4,695,251 (Randklev); and submicrometer silica particles (e.g., pyrogenic silicas such as the "AEROSIL" Series "OX 50", "130", "150" and "200" silicas sold by Degussa Akron, Ohio and "CAB-O-SIL M5" silica sold by Cabot Corp. Tuscola, Ill.) and non-vitreous microparticles of the type described in U.S. Pat. No. 4,503,169 (Randklev). Silane-treated zirconia-silica (Zr—Si) filler particles are especially useful in certain embodiments.

Metallic filler particles may also be incorporated, such as metal filler particles made from a pure metal such as those of Groups 4, 5, 6, 7, 8, 11, or 12, aluminum, indium, and thallium of Group 13, and tin and lead of Group 14, or alloys thereof, where the elements from the recited Groups are found in the 8 Jan. 2016 version of the IUPAC Periodic Table. Conventional dental amalgam alloy powders, typically mixtures of silver, tin, copper, and zinc, may also optionally be incorporated. The metallic filler particles preferably have a number average particle size diameter of about 1 micrometer to about 100 micrometers, more preferably 1 micrometer to about 50 micrometers. Mixtures of these filler particles are also contemplated, as well as combination filler particles made from organic and inorganic materials.

Preferably, the composite material can include, when present, up to 15 wt. % of nanoparticles as the filler particles based on the total weight of the composite material. For example, the composite material can include 2 to 15 wt. % or 2 to 12 wt. % of nanoparticles as the filler particles based on the total weight of the composite material. As defined herein, the nanoparticles are discrete non-fumed metal oxide nanoparticles. As discussed herein, for a given combination of components that forms the composite material the wt. % of each of the components adds to 100 wt. % (wt. % based on the total weight of the composite material). Examples of discrete non-fumed metal oxide nanoparticles include discrete non-fumed heavy metal oxide nanoparticles. In addition, the discrete non-fumed metal oxide nanoparticles can include both discrete non-fumed heavy metal oxide nanoparticles and discrete non-fumed non-heavy metal oxide nanoparticles. Examples of discrete non-fumed non-heavy metal oxide nanoparticles include nanosilica, while examples of discrete non-fumed heavy metal oxide nanoparticles include zirconia, yttria and lanthana particles. Discrete non-fumed heavy metal oxide nanoparticles may be prepared from heavy metal oxide sols as described according to U.S. Pat. No. 6,736,590 (Kolb et al.) or U.S. Pat. No. 7,429,422 (Davidson et al.). Discrete non-fumed non-heavy metal oxides may be purchased as colloidal silica. The discrete non-fumed nanoparticles of silica may be prepared from dispersions, sols, or solutions of at least one precursor. Processes of this nature are described, for example, in U.S. Pat. No. 4,503,169 (Randklev) and GB Patent No. 2291053 B (Noritake, et al.). The discrete non-fumed metal oxide nanoparticles may also be surface treated with, for example, a silane prior to mixing with a polymerizable component.

The discrete non-fumed metal oxide nanoparticles are typically finely divided with a unimodal or polymodal (e.g., bimodal) particle size distribution. The maximum particle size (the largest dimension of a particle, generally, the diameter) of the discrete non-fumed metal oxide nanoparticles is typically 5 nm to 200 nm, more typically 5 nm to 100 nm, and most typically 5 nm to 80 nm.

Other suitable filler particles are disclosed in U.S. Pat. No. 6,387,981 (Zhang, et al.); U.S. Pat. No. 6,572,693 (Wu, et al.); U.S. Pat. No. 6,730,156 (Windisch); and U.S. Pat. No. 6,899,948 (Zhang); U.S. Pat. No. 7,022,173 (Cummings, et al.); U.S. Pat. No. 6,306,926 (Bretscher, et al.); U.S. Pat. No. 7,030,049 (Rusin, et al.); U.S. Pat. No. 7,160,528 (Rusin); U.S. Pat. No. 7,393,882 (Wu, et al.); U.S. Pat. No. 6,730,156 (Windisch, et al.); U.S. Pat. No. 6,387,981 (Zhang, et al.); U.S. Pat. No. 7,090,722 (Budd, et al.); U.S. Pat. No. 7,156,911 (Kangas, et al.); U.S. Pat. No. 7,361,216 (Kolb, et al.); as well as in International Publication No. WO 03/063804 (Wu, et al.), incorporated herein by reference. Filler particles described in these references include nanosized silica particles, nanosized metal oxide particles, and combinations thereof. Nanofillers are also described in U.S. Pat. No. 7,085,063 (Kangas, et al.); U.S. Pat. No. 7,090,721 (Craig, et al.) and U.S. Pat. No. 7,649,029 (Kolb, et al.); and U.S. Patent Publication Nos. 2010/0089286 (Craig, et al); US 2011/0196062 (Craig, et al), all incorporated herein by reference.

As discussed herein, the surface of the filler particles may, optionally, be treated with a surface treatment, as discussed herein, in order to enhance the bond between the filler and the polymerizable component. In addition, the ceramic fibers and filler particles, when filler particles are present, may be modified with more than one (e.g., two or more) of the surface treatments discussed herein (e.g., coupling agents and/or surface treatments). For example, the same surface treatments may be used for each of the ceramic fibers, while different surface treatments may be used for the filler particles, when present. Different surface treatments may also be used for two or more groups of the ceramic fibers and filler particles, when present in the composite material. For example, the ceramic fibers to be used in the composite material can include a first group of the ceramic fibers that have a surface treatment that is compositionally different than a second group of the ceramic fibers used in the composite material.

As discussed herein, to achieve good aesthetics in a composite material, the optical properties of the components of the composite need to be highly matched. Examples of such optical properties for the components include not only the shade and the color of the components, but also how well the refractive index of the fillers (e.g., the ceramic fibers) match the refractive index of the hardened polymerizable component. Matching the refractive index of the components helps to minimize the scattering of light as it passes through the material, thereby helping to provide a more translucent material. So, for example, the ceramic fibers of the present disclosure preferably have a refractive index value within 0.1 or less of the refractive index of the hardened polymerizable component. More preferable is where the ceramic fibers of the present disclosure preferably have a refractive index value within 0.05 or less of the refractive index of the hardened polymerizable component. Most preferable is where the ceramic fibers of the present disclosure preferably have a refractive index value within 0.005 or less of the refractive index of the hardened polymerizable component.

Examples of refractive index values for the ceramic fibers include ceramic fibers have a refractive index value of 1.40 to 1.65. Preferably, the refractive index value of the ceramic fibers is 1.50 to 1.58. Most preferably, the refractive index value of the ceramic fibers is 1.51 to 1.56. A preferred method for adjusting the refractive index of the ceramic fibers is by altering the ratio of oxide of silicon to ceramic metal oxide. The ceramic fibers refractive index can be approximately predicted by interpolation based on a comparison of the relative volume percent of silica to ceramic metal oxide in the starting mixtures. When additional filler(s) are used with the ceramic fibers their refractive index values can also be matched within the ranges provided herein.

The composite material of the present disclosure can be prepared by combining all the various components using conventional mixing techniques. The resulting composite material may optionally contain additional fillers (in addition to the ceramic fibers and nanoclusters), solvents, water, and/or other additives as described herein. Typically, photopolymerizable composite materials of the disclosure are prepared by admixing, under "safe light" conditions, the components of the composite material. Suitable inert solvents may be employed if desired when affecting this mixture. A solvent may be used which does not react appreciably with the components of the composite material.

Examples of suitable solvents include alcohols (e.g., propanol, ethanol), ketones (e.g., acetone, methyl ethyl ketone), esters (e.g., ethyl acetate), other nonaqueous solvents (e.g., dimethylformamide, dimethylacetamide, dimethylsulfoxide, 1-methyl-2-pyrrolidinone)), or mixtures thereof. If desired, the composite material of the disclosure may contain additives such as indicators, dyes (including photobleachable dyes), pigments, inhibitors, accelerators, viscosity modifiers, wetting agents, antioxidants, tartaric acid, chelating agents, buffering agents, stabilizers, diluents, and other similar ingredients that will be apparent to those skilled in the art. Surfactants, for example, nonionic surfactants, cationic surfactants, anionic surfactants, and combinations thereof, may optionally be used in the compositions. Useful surfactants include non-polymerizable and polymerizable surfactants.

Additionally, medicaments or other therapeutic substances can be optionally added to the composite material. Examples include, but are not limited to, fluoride sources, whitening agents, anticaries agents (e.g., xylitol), remineralizing agents (e.g., calcium phosphate compounds and other calcium sources and phosphate sources), enzymes, breath fresheners, anesthetics, clotting agents, acid neutralizers, chemotherapeutic agents, immune response modifiers, thixotropes, polyols, anti-inflammatory agents, antimicrobial agents, antifungal agents, agents for treating xerostomia, desensitizers, and the like, of the type often used in dental restorative materials. Combinations of any of the above additives may also be employed. The selection and amount of any one such additive can be selected by one of skill in the art to accomplish the desired result without undue experimentation.

The amounts and types of each ingredient in the composite material can be adjusted to provide the desired physical and handling properties before and after polymerization. For example, the polymerization rate, polymerization stability, fluidity, compressive strength, tensile strength and durability of the dental restorative material typically may be adjusted, in part, by altering the types and amounts of polymerization initiator(s) and the loading and particle size distribution of filler(s). Such adjustments typically are carried out empirically based on previous experience with composite materials. When the composite material is used in a dental application, any tooth surface receiving the composite material can optionally be pre-treated with a primer and/or an adhesive by methods known to those skilled in the art.

The composite material can be supplied in a variety of forms including one-part systems and multi-part systems, e.g., two-part paste/paste systems. Other forms employing multi-part combinations (i.e., combinations of two or more parts), each of which is in the form of a powder, liquid, gel, or paste are also possible. The various components of the composite material may be divided up into separate parts in whatever manner is desired; however, in a redox multi-part system, one part typically contains the oxidizing agent and another part typically contains the reducing agent, though it is possible to combine the reducing agent and oxidizing agent in the same part of the system if the components are kept separated, for example, through use of microencapsulation.

Hardened composite materials according to at least certain embodiments of the present disclosure preferably exhibit at least one desirable physical property. These physical properties include the following: flexural strength, diametral tensile strength (DTS), fracture toughness, polish retention, and wear resistance. Preferably, the article exhibits at least two different desirable physical properties, more preferably at least three different desirable physical properties, even more preferably at least flexural strength, DTS, and fracture toughness, and most preferably at least flexural strength, DTS, fracture toughness, and polish retention. The typical amounts of these properties are described below.

In some embodiments, the composite material forms a hardened composite material having a DTS of 65 megapascals (MPa) or greater, 66 MPa or greater, 67 MPa or greater, 68 MPa or greater, 69 MPa or greater, 70 MPa or greater, 71 MPa or greater, 72 MPa or greater, 73 MPa or greater, 74 MPa or greater, 75 MPa or greater, 76 MPa or greater, 77 MPa or greater, or even 78 MPa or greater. The DTS can be determined using the "Diametral Tensile Strength Test Method" described in detail in the Examples below.

In some embodiments, the composite material forms a hardened composite material having a flexural strength of 170 MPa or greater, 172 MPa or greater, 174 MPa or greater, 176 MPa or greater, 178 MPa or greater, 180 MPa or greater, 182 MPa or greater, 184 MPa or greater, 186 MPa or greater, 188 MPa or greater, 190 MPa or greater, 192 MPa or greater, 194 MPa or greater, 196 MPa or greater, 198 MPa or greater, 200 MPa or greater, 202 MPa or greater, 204 MPa or greater, 206 MPa or greater, or even 208 MPa or greater. The flexural strength can be determined using the "Flexural Strength Test Method" described in detail in the Examples below. In some embodiments, the composite material forms a hardened composite material having a fracture toughness of 2.50 megapascals·square root meters (MPa·m$^{1/2}$) or greater, 2.55 MPa·m$^{1/2}$ or greater, 2.60 MPa·m$^{1/2}$ or greater, 2.65 MPa·m$^{1/2}$ or greater, 2.70 MPa·m$^{1/2}$ or greater, 2.75 MPa·m$^{1/2}$ or greater, 2.80 MPa·m$^{1/2}$ or greater, 2.85 MPa·m$^{1/2}$ or greater, 2.90 MPa·m$^{1/2}$ or greater, 2.95 MPa·m$^{1/2}$ or greater, 3.00 MPa·m$^{1/2}$ or greater, 3.05 MPa·m$^{1/2}$ or greater, 3.10 MPa·m$^{1/2}$ or greater, or 3.15 MPa·m$^{1/2}$ or greater. The fracture toughness can be determined using the "Fracture Toughness Test Method" described in detail in the Examples below.

In select embodiments, the composite material forms a hardened composite material having each of a DTS of 65 MPa or greater, a flex strength of 170 MPa or greater, and a fracture toughness of 2.50 MPa·m$^{1/2}$ or greater.

Advantageously, use of small diameter and short length ceramic fibers assists in obtaining desirable polish retention in hardened composite material. In some embodiments, the composite material forms a hardened composite material having a polish retention of 40 gloss units or greater at 60° after 6000 brush cycles. The polish retention is determined using the "Gloss Retention after Toothbrush Abrasion Test Method" described in detail in the Examples below. Preferably, hardened composite materials according to at least some embodiments of the present disclosure exhibit a polish retention of 40 gloss units or greater 60° after 6000 brush cycles in combination with at least one of a DTS of 65 MPa or greater, a flex strength of 170 MPa or greater, or a fracture toughness of 2.50 MPa·m$^{1/2}$ or greater, and more preferably in combination with all three.

In some embodiments, a ratio of a wear resistance of a hardened composite material formed of the composite material to a wear resistance of a hardened polymerizable component formed of a control composite material is 2.0 or less, 1.9 or less, 1.8 or less, 1.7 or less, 1.6 or less, 1.5 or less, 1.4 or less, 1.3 or less, or even 1.2 or less. The control composite material has the same composition as the composite material except for being free of ceramic fibers.

In a second aspect, a dental product is provided. The dental product is made by hardening the composite material according to the first aspect described in detail above. Hardening the composite material can be accomplished based on the type of dental product being produced. For example, the composite material can be hardened, when appropriate, using heat, light, microwave, e-beam, fusing or chemical cure. Once hardened, the dental product and/or dental mill blank of the present disclosure can be trimmed if necessary; and optionally, mounted on a holder stub or post if necessary. The dental product can be selected from the group consisting of a dental restorative (e.g., a sealant, an inlay, an onlay or a bridge), a dental adhesive, a dental mill blank, a dental cement, a dental prostheses, an orthodontic device, an orthodontic adhesive, a dental casting material, artificial crowns, anterior fillings, posterior fillings, and cavity liners or a dental coating.

The dental mill blank of the present disclosure is a block (three dimensional article) of material from which a dental article can be machined. A dental mill blank may have a size suitable for the machining of one or more dental articles. The dental mill blank of the present disclosure can also include a mounting post or frame to facilitate affixation of the blank in a milling machine for milling a dental restorative. A mounting post or frame functions as handle by which a blank is held as it undergoes the milling process. An example of a device for such milling processes can include a CAM machine controlled by data provided by a CAD system (e.g., a CNC machine) for the shape of the desired dental article. These machines produce dental prostheses by cutting, milling, and grinding the near-exact shape and morphology of a required restorative with greater speed and lower labor requirements than conventional hand-made procedures. By using a CAD/CAM milling device, the prosthesis can be fabricated efficiently and with precision. Other machining process can include abrading, polishing, controlled vaporization, electronic discharge milling (EDM), cutting by water jet or laser or other method of cutting, removing, shaping or milling material. After milling, some degree of finishing, polishing and adjustment may be necessary to obtain a custom fit into the mouth and/or aesthetic appearance.

In a third aspect, a method of making a composite material is provided. The method includes obtaining a plurality of components according to the first aspect described in detail above, and admixing the plurality of components to make the composite material. The components of the composite material can be mixed and clinically applied using conventional techniques. A curing light is generally required for the initiation of photopolymerizable composite materials. The composite material may be in the form of composites or restoratives that adhere very well to dentin and/or enamel. Optionally, a primer layer can be used on the tooth tissue on which the composite material is used.

In a fourth aspect, a method of using a composite material is provided. The method includes placing the composite material according to the first aspect described in detail above, near or on a tooth surface; changing the shape of the composite material near or on the tooth surface; and hardening the composite material. Changing the shape of the composite material near or on the tooth surface can include shaping the composite material into a dental product selected from the group consisting of a dental prostheses, an orthodontic device, a dental crown, an anterior filling, a posterior filing or a cavity liner. These steps can be followed sequentially or in a different order. For example, in a preferred embodiment where the dental restorative material is a dental mill blank or a prosthesis, the hardening step is generally completed prior to changing the topography of the material. Changing the topography of the material can be accomplished in various ways, including manual manipulation using hand held instruments, or by machine or computer aided apparatus, such as a CAD/CAM milling machine in the case of prostheses and dental mill blanks. Optionally, a finishing step can be performed to polish, finish, or apply a coating on the dental restorative material.

The components of the composite material can be included in a kit, where the contents of the composite material are packaged in at least one container to hold the composite material and allow for storage of the components until they are needed. Hence, in a fifth aspect, a kit is provided. The kit includes a composite material according to the first aspect as described in detail above; and at least one container to hold the composite material. More than one of the composite materials discussed herein can be included in the kit. In addition to the composite material(s) of the present disclosure, the kit can also include at least one dental component selected from the group of a cement, an adhesive, an abrasive, a polishing paste, an instrument, software, a mill, a CAD/CAM system, a composite, a porcelain, a stain, a bur, an impression material, a dental mill blank, or a combination thereof.

The features and advantages of this disclosure are further illustrated by the following examples, which are in no way intended to be limiting thereof. The particular materials and amounts thereof recited in these examples, as well as other conditions and details, should not be construed to unduly limit this disclosure. Unless otherwise indicated, all parts and percentages are on a weight basis, all water is deionized water, and all molecular weights are weight average molecular weight.

SELECT EMBODIMENTS OF THE DISCLOSURE

Embodiment 1 is a composite material. The composite material includes 20 to 40 weight percent (wt. %) of a polymerizable component; 6 to 40 wt. % of ceramic fibers; and 30 to 70 wt. % of nanoclusters. The wt. % values of the composite material are based on a total weight of the composite material and total to a value of 100 wt. %. Each of the ceramic fibers has a diameter and a length, the ceramic fibers have an arithmetic mean diameter of 0.3 micrometers to 5 micrometers, and the length of fifty percent of the ceramic fibers, based on a total number of the ceramic fibers, is at least 10 micrometers and the length of ninety percent of the ceramic fibers, based on the total number of the ceramic fibers, is no greater than 500 micrometers.

Embodiment 2 is the composite material of embodiment 1, wherein an aspect ratio of an arithmetic mean length of the ceramic fibers to an arithmetic mean diameter of the ceramic fibers is at least 10:1 (mean length:mean diameter).

Embodiment 3 is the composite material of embodiment 2, wherein the aspect ratio is up to 150:1 (mean length:mean diameter).

Embodiment 4 is the composite material of any of embodiments 1-3, wherein the ceramic fibers have an arithmetic mean diameter of 0.3 to 3 micrometers.

Embodiment 5 is the composite material of any of embodiments 1-3, wherein the arithmetic mean diameter of the ceramic fibers is 2 to 5 micrometers.

Embodiment 6 is the composite material of any of embodiments 1-5, wherein the ceramic fibers are at least partially amorphous ceramic fibers.

Embodiment 7 is the composite material of embodiment 6, wherein the ceramic fibers are completely amorphous ceramic fibers.

Embodiment 8 is the composite material of any of embodiments 1-7, wherein the ceramic fibers have an arithmetic mean length of 50 micrometers to 250 micrometers.

Embodiment 9 is the composite material of any of embodiments 1-8, wherein the length of ninety percent of the ceramic fibers, based on the total number of the ceramic fibers, is no greater than 200 micrometers.

Embodiment 10 is the composite material of any of embodiments 1-9, wherein the composite material includes 6 to 30 wt. % or 10 to 20 wt. % of the ceramic fibers based on the total weight of the composite material.

Embodiment 11 is the composite material of any of embodiments 1-10, wherein the ceramic fibers include alumina fibers, alumina-silica fibers, aluminum borosilicate fibers, zirconia-silica fibers, borosilicate glass fibers, silicate fibers modified with alkalis or alkaline earths, fused silica fibers, leached silica fibers, quartz fibers, fiberglass, or combinations thereof. Embodiment 12 is the composite material of any of embodiments 1-10, wherein the ceramic fibers are composed of alumina-silica fibers, borosilicate glass fibers, or combinations thereof.

Embodiment 13 is the composite material of any of embodiments 1-12, wherein the composite material includes up to 15 wt. % of nanoparticles.

Embodiment 14 is the composite material of embodiment 13, wherein the composite material includes 2 to 12 wt. % of nanoparticles.

Embodiment 15 is the composite material of embodiment 13 or embodiment 14, wherein the nanoparticles are discrete non-fumed metal oxide nanoparticles.

Embodiment 16 is the composite material of embodiment 15, wherein the discrete non-fumed metal oxide nanoparticles are discrete non-fumed heavy metal oxide nanoparticles.

Embodiment 17 is the composite material of embodiment 16, wherein the discrete non-fumed metal oxide nanoparticles include both discrete non-fumed heavy metal oxide nanoparticles and discrete non-fumed non-heavy metal oxide nanoparticles.

Embodiment 18 is the composite material of any of embodiments 1-17, wherein the composite material includes 35 to 64 wt. % of nanoclusters.

Embodiment 19 is the composite material of any of embodiments 1-17, wherein the polymerizable component forms a hardened polymerizable component having a refractive index, and wherein the ceramic fibers have a refractive index value within 0.1 or less of the refractive index of the hardened polymerizable component.

Embodiment 20 is the composite material of embodiment 19, wherein the ceramic fibers have a refractive index value within 0.05 or less of the refractive index of the hardened polymerizable component.

Embodiment 21 is the composite material of any of embodiments 1-20, wherein the ceramic fibers have a refractive index value of 1.40 to 1.65.

Embodiment 22 is the composite material of embodiment 21, wherein the refractive index value of the ceramic fibers is 1.51 to 1.56.

Embodiment 23 is the composite material of any of embodiments 1-22, wherein the polymerizable component is an ethylenically unsaturated compound.

Embodiment 24 is the composite material of any of embodiments 1-23, further including an initiator selected from the group consisting of a free radical initiator, a photoinitiator, a thermally activated initiator, or a combination thereof.

Embodiment 25 is the composite material of any of embodiments 1-24, further including a coupling agent, wherein the coupling agent provides a chemical bond between the ceramic fibers and the polymerizable component.

Embodiment 26 is the composite material of embodiment 25, wherein the coupling agent is selected from the group consisting of an organosilane coupling agent, a titanate coupling agent, a zirconate coupling agent, an acidic coupling agent, or a combination thereof.

Embodiment 27 is the composite material of any of embodiments 1-26, wherein the composite material is hardened to become any one of a dental restorative, a dental adhesive, a dental mill blank, a dental cement, a dental prostheses, an orthodontic device, an orthodontic adhesive, a dental casting material, or a dental coating.

Embodiment 28 is the composite material of any of embodiments 1-27, wherein the nanoclusters are silica-zirconia nanoclusters.

Embodiment 29 is the composite material of embodiment 28, wherein the silica-zirconia nanoclusters are formed by primary particles, and wherein each of the primary particles has a diameter of 1 nanometer to 200 nanometers.

Embodiment 30 is the composite material of any of embodiments 1-29, wherein the composite material forms a hardened composite material having a diametral tensile strength (DTS) of 65 megapascals (MPa) or greater.

Embodiment 31 is the composite material of embodiment 30, wherein the composite material forms a hardened composite material having a DTS of 75 MPa or greater.

Embodiment 32 is the composite material of any of embodiments 1-31, wherein the composite material forms a hardened composite material having a flexural strength of 170 MPa or greater.

Embodiment 33 is the composite material of embodiment 32, wherein the composite material forms a hardened composite material having a flexural strength of 180 MPa or greater.

Embodiment 34 is the composite material of any of embodiments 1-33, wherein the composite material forms a hardened composite material having a fracture toughness of 2.50 megapascals·square root meters (MPa·m$^{1/2}$) or greater.

Embodiment 35 is the composite material of embodiment 34, wherein the composite material forms a hardened composite material having a fracture toughness of 2.80 MPa·m$^{1/2}$ or greater.

Embodiment 36 is the composite material of any of embodiments 1-30, wherein the composite material forms a hardened composite material having each of a DTS of 65 MPa or greater, a flexural strength of 170 MPa or greater, and a fracture toughness of 2.50 MPa·m$^{1/2}$ or greater.

Embodiment 37 is the composite material of any of embodiments 1-36, wherein the composite material forms a hardened composite material having a polish retention of 40 gloss units or greater at 60° after 6000 brush cycles.

Embodiment 38 is the composite material of any of embodiments 1-37, wherein a ratio of a wear resistance of a hardened composite material formed of the composite material to a wear resistance of a hardened composite material formed of a control composite material is 2.0 or less, wherein the control composite material has the same composition as the composite material except for being free of ceramic fibers.

Embodiment 39 is a dental product. The dental product is made by hardening the composite material of any of the preceding embodiments 1-38.

Embodiment 40 is the dental product of embodiment 39, wherein the dental product is selected from the group consisting of a dental restorative, a dental adhesive, a dental mill blank, a dental cement, a dental prostheses, an orthodontic device, an orthodontic adhesive, a dental casting material, artificial crowns, anterior fillings, posterior fillings, cavity liners, or a dental coating.

Embodiment 41 is a method of making a composite material. The method includes obtaining a plurality of components and admixing the plurality of components to make the composite material. The components include 20 to 40 wt. % of a polymerizable component; 6 to 40 wt. % of ceramic fibers; and 30 to 70 wt. % of nanoclusters. The wt. % values of the composite material are based on a total weight of the composite material and total to a value of 100 wt. %. Each of the ceramic fibers has a diameter and a length, the ceramic fibers have an arithmetic mean diameter of 0.3 micrometers to 5 micrometers, and the length of fifty percent of the ceramic fibers, based on a total number of the ceramic fibers, is at least 10 micrometers and the length of ninety percent of the ceramic fibers, based on the total number of the ceramic fibers, is no greater than 500 micrometers.

Embodiment 42 is the method of embodiment 41, wherein the plurality of components further includes up to 15 wt. % of nanoparticles based on the total weight of the composite material.

Embodiment 43 is the method of embodiment 42, wherein the composite material includes 2 to 12 wt. % of nanoparticles.

Embodiment 44 is the method of claim 42 or claim 43, wherein the nanoparticles are discrete non-fumed metal oxide nanoparticles.

Embodiment 45 is the method of embodiment 44, wherein the discrete non-fumed metal oxide nanoparticles are discrete non-fumed heavy metal oxide nanoparticles.

Embodiment 46 is the method of embodiment 45, wherein the discrete non-fumed metal oxide nanoparticles include both discrete non-fumed heavy metal oxide nanoparticles and discrete non-fumed non-heavy metal oxide nanoparticles.

Embodiment 47 is the method of any of embodiments 41-46, wherein an aspect ratio of an arithmetic mean length of the ceramic fibers to an arithmetic mean diameter of the ceramic fibers is at least 10:1 (mean length:mean diameter).

Embodiment 48 is the method of embodiment 47, wherein the aspect ratio is up to 150:1 (mean length:mean diameter).

Embodiment 49 is the method of any of embodiments 41-48, wherein the ceramic fibers have an arithmetic mean diameter of 0.3 to 3 micrometers.

Embodiment 50 is the method of any of embodiments 41-48, wherein the arithmetic mean diameter of the ceramic fibers is 2 to 5 micrometers.

Embodiment 51 is the method of any of embodiments 41-50, wherein the ceramic fibers are at least partially amorphous ceramic fibers.

Embodiment 52 is the method of embodiment 51, wherein the ceramic fibers are completely amorphous ceramic fibers.

Embodiment 53 is the method of any of embodiments 41-52, wherein the ceramic fibers have an arithmetic mean length of 50 micrometers to 250 micrometers.

Embodiment 54 is the method of any of embodiments 41-53, wherein the length of ninety percent of the ceramic fibers, based on the total number of the ceramic fibers, is no greater than 500 micrometers.

Embodiment 55 is the method of any of embodiments 41-54, wherein the composite material includes 6 to 30 wt. % or 10 to 20 wt. % of the ceramic fibers based on the total weight of the composite material.

Embodiment 56 is the method of any of embodiments 41-55, wherein the ceramic fibers comprise alumina fibers, alumina-silica fibers, aluminum borosilicate fibers, zirconia-silica fibers, borosilicate glass fibers, silicate fibers modified with alkalis or alkaline earths, fused silica fibers, leached silica fibers, quartz fibers, fiberglass, or combinations thereof.

Embodiment 57 is the method of any of embodiments 41-56, wherein the ceramic fibers are composed of alumina-silica fibers, borosilicate glass fibers, or combinations thereof. Embodiment 58 is the method of any of embodiments 41-57, wherein the composite material includes 35 to 64 wt. % of nanoclusters.

Embodiment 59 is the method of any of embodiments 41-58, wherein the ceramic fibers have a refractive index value of 1.40 to 1.65.

Embodiment 60 is the method of embodiment 59, wherein the refractive index value of the ceramic fibers is 1.51 to 1.56.

Embodiment 61 is the method of any of embodiments 41-60, wherein the polymerizable component is an ethylenically unsaturated compound.

Embodiment 62 is the method of any of embodiments 41-61, wherein the plurality of components further includes an initiator selected from the group consisting of a free radical initiator, a photoinitiator, a thermally activated initiator, or a combination thereof.

Embodiment 63 is the method of any of embodiments 41-62, wherein the plurality of components further includes a coupling agent, wherein the coupling agent provides a chemical bond between the ceramic fibers and the polymerizable component.

Embodiment 64 is the method of embodiment 63, wherein the coupling agent is selected from the group consisting of an organosilane coupling agent, a titanate coupling agent, a zirconate coupling agent, an acidic coupling agent, or a combination thereof.

Embodiment 65 is the method of any of embodiments 41-64, wherein the nanoclusters are silica-zirconia nanoclusters.

Embodiment 66 is the method of embodiment 65, wherein the silica-zirconia nanoclusters are formed by primary particles, and wherein each of the primary particles has a diameter of 1 nanometer to 200 nanometers.

Embodiment 67 is the method of any of embodiments 41-66, further including hardening the composite material to form a dental product.

Embodiment 68 is the method of embodiment 67, wherein the dental product has a refractive index, and wherein the ceramic fibers have a refractive index value within 0.1 or less of the refractive index of the dental product.

Embodiment 69 is the method of embodiment 68, wherein the ceramic fibers have a refractive index value within 0.05 or less of the refractive index of the hardened polymerizable component.

Embodiment 70 is the method of any of embodiments 67 to 69, wherein the dental product includes any one of a dental restorative, a dental adhesive, a dental mill blank, a dental cement, a dental prostheses, an orthodontic device, an orthodontic adhesive, a dental casting material, or a dental coating.

Embodiment 71 is a method of using a composite material. The method includes placing the composite material according any of embodiments 1-36 near or on a tooth surface; changing the shape of the composite material near or on the tooth surface; and hardening the composite material.

Embodiment 72 is the method of embodiment 71, where changing the shape of the composite material near or on the tooth surface includes shaping the composite material into a dental product selected from the group consisting of a dental prostheses, an orthodontic device, a dental crown, an anterior filling, a posterior filing, or a cavity liner.

Embodiment 73 is the method of embodiment 71 or embodiment 72, further including polishing the composite material after hardening the composite material.

Embodiment 74 is a kit. The kit includes a composite material of any of embodiments 1-36; and at least one container to hold the composite material.

Embodiment 75 is the kit of embodiment 77, further including at least one dental component selected from the group of a cement, an adhesive, an abrasive, a polishing paste, an instrument, software, a mill, a CAD/CAM system, a composite, a porcelain, a stain, a bur, an impression material, a dental mill blank or a combination thereof.

EXAMPLES

Advantages and embodiments of this invention are further illustrated by the following examples, but the particular materials and amounts thereof recited in these examples, as well as other conditions and details, should not be construed to unduly limit this invention. All parts and percentages are by weight unless otherwise indicated.

Test Methods

Fiber Length Measurement

The length of ceramic fibers was determined using an optical microscope (Keyence VHX Digital Microscope System, Keyence Corporation, Itasca, Ill.) with analytic software. Samples were prepared by spreading representative samplings of the ceramic fiber on double sided tape attached to a glass slide and measuring the lengths of at least 50 ceramic fibers at 100× magnification. The mean length and corresponding standard deviation (SD) were calculated and recorded.

Fiber Diameter Measurement

The diameter of ceramic fibers was determined using one of two methods. For fibers with diameters greater than 2 micrometers, a Keyence VHX digital microscope was used at 1,000× magnification. Samples were prepared by spreading representative samplings of the ceramic fiber on double sided tape attached to a glass slide and measuring the diameters of at least 50 ceramic fibers at 1,000× magnification. For fibers less than 2 micrometers, a Zeiss Scanning Electron Microscope (Carl Zeiss Microscopy LLC, Thornbush, N.Y.) was used at a magnification of 3,000× to 15,000× with about 500-100 individual fibers in the field of view. Fiber samples were adhered to microscope stubs with conductive double sided tape and coated with Au—Pd. About 40-100 individual fibers were measured for each sample. The mean diameter was calculated and recorded.

Flexural Strength Test Method

Each test specimen was prepared by extruding uncured composite material into a 2 mm×2 mm×25 mm quartz glass mold to form a test bar. The test bar of the composite material was cured in the quartz glass mold using two XL3000 dental cure lights (3M Corporation, Maplewood, Minn.). The exit window of one light was placed over the center of the test bar and the composite material was cured for 20 seconds. Next, using the two lights in tandem, the exit windows of the lights were placed over the uncured ends of the test bar and the composite material on each end of the bar was simultaneously cured for 20 seconds. The test bar was flipped and the cure protocol was repeated. The cured test bar of the composite material was pushed out of the quartz glass mold. The cured test bar of composite material was submerged in deionized water (37° C.) for about 24 hours prior to testing.

Flexural Strength of each cured test bar of the composite material was measured using an Instron tester (Instron 5944, Instron Corporation, Canton, Mass.) according to ANSI/ADA (American National Standard/American Dental Association) specification No. 27 (1993) at a crosshead speed of 0.75 mm/minute and a span of 20 mm. For each test specimen, five test bars were evaluated and the mean Flexural Strength (MPa, megapascals) was reported.

Fracture Toughness Test Method

Each test specimen was prepared by extruding uncured composite material into a 3 mm×5 mm×25 mm quartz glass mold to form a test bar. The test bar of the composite material was cured in the quartz glass mold using two XL3000 dental cure lights (3M Corporation). The exit window of one light was placed over the center of the test bar and the composite material was cured for 20 seconds. Next, using the two lights in tandem, the exit windows of the lights were placed over the uncured ends of the test bar and the composite material on each end of the bar was simultaneously cured for 20 seconds. The test bar was flipped and the cure protocol was repeated. The test bar of the cured composite material was pushed out of the quartz glass mold. A notch was cut in the center of the test bar using a wafering blade with a kerf of 0.15 mm and an ISOMET Low Speed Saw (Buehler, Lake Bluff, Ill.). The notch was approximately 2 mm deep. The cured test bar of composite material was submerged in deionized water (37° C.) for about 24 hours prior to testing.

Fracture Toughness of each cured test bar was measured using an Instron tester (Instron 5944, Instron Corporation) with a crosshead speed of 0.75 mm/minute. The toughness was calculated per ASTM 399-05. For each test specimen, five test bars were evaluated and the mean Flexural Strength (MPa·m$^{1/2}$) was reported.

Diametral Tensile Strength Test Method

Each test specimen was prepared by extruding uncured composite material into a 4 mm inner diameter glass tube and capping the tube at both ends with silicone rubber plugs. The filled tube was compressed axially at approximately 40 psi for five minutes. The tube was then light cured for one minute with an XL1500 dental curing light (3M Corporation) with continuous rotation of the tube. The tube of cured composite material was then cut with a diamond saw to form individual 2 mm sections. The cured composite material was removed from each section to provide individual test disks. Each test disk was submerged in deionized water (37° C.) for about 24 hours prior to testing.

Diametral Tensile Strength of each cured test disk of composite material was measured using an Instron tester (Instron 5966, Instron Corporation) with a crosshead speed of 1 mm/minute according to ISO Specification 7489 (or American Dental Association (ADA) Specification No. 27). For each test specimen, nine disks were evaluated and the mean Diametral Tensile Strength (MPa) was reported.

Gloss Retention after Toothbrush Abrasion Test Method

Samples of uncured composite were formed into 2 mm thick×21 mm long×10 mm wide tiles using a stainless steel mold. The uncured composite was pressed flat between sheets of polyester film in a Carver Press (Wabash, Ind.) at 6000 to 10,000 psi and cured for 20 seconds using an LED (light emitting diode) array with 455 nm wavelength, 850 mW/cm$^2$ intensity (Clear Stone Technology, Hopkins, Minn.: Control Unit CF2000, LED array JL2-455F-90). The resulting sample tile was removed from the mold and polished to a high gloss using an Ecomet 4 Variable Speed Grinder-Polisher fit with an Automet 2 Power Head (Buehler). High gloss was achieved through the use of consecutively finer grinding and polishing media. First, 320 grit silicon carbide sandpaper was used followed by 600 grit silicon carbide sandpaper (sandpaper from the 3M Corporation). Polishing was continued with a 9 micrometer diamond paste, followed by a 3 micrometer paste, and finally a 0.05 micrometer polishing slurry (polishing paste and slurry purchased from Buehler). Each polished tile was stored for about 24 hours submerged in 37° C. water.

The gloss retention of each tile was measured by challenging the polished surface with toothbrush abrasion. The tile was affixed in a jig, gloss side up. The initial gloss (sixty degree gloss) was measured using a Novo-Curve glossmeter (Rhopoint Instrument, St. Leonards-on-the-Sea, East Sussex, UK) according to ASTM D2457. The jig was placed in a well in an automated brushing machine where 5 mL of abrasive slurry consisting of 1:1 Crest Regular Toothpaste (Procter & Gamble Company, Cincinnati, Ohio) and water was placed over the tile. The tile was then brushed under a load of 450 gf (gram-force) with a 47 tuft Acclean toothbrush (Henry Schein, Melville, N.Y.). The tiles were subjected to 6000 total brush cycles, with the gloss measured after every 1500 brush cycles. Five milliliters of fresh slurry was added to the tile after each intermediate gloss measurements. For each sample, at least three tile surfaces were evaluated and the mean gloss value (sixty degree gloss) was reported.

Materials

"BisEMA-6" refers to ethoxylated (6 mole ethylene oxide) bisphenol A dimethacrylate as further described in U.S. Pat. No. 6,030,606, obtained from the Sartomer Company (Exton, Pa.) as "CD541".

"BisGMA" refers to 2,2-bis[4-(2-hydroxy-3-methacryloyloxypropoxy)phenyl]propane (also referred to as bisphenol A diglycidyl ether methacrylate), CAS Reg. No. 1565-94-2.

"BHT" refers to butylated hydroxytoluene (2,6-di-tert-butyl-4-methylphenol), CAS Reg. No. 128-37-0.

"BZT" refers to 2-(2'-hydroxy-5'-methacryloxyethylphenyl)-2H-benzotriazole, CAS Reg. No. 96478-09-0, obtained from Ciba Specialty Chemicals Corporation Incorporated (Tarrytown, N.Y.) as "TINUVIN R 796".

"CPQ" refers to camphorquinone, CAS Reg. No. 10373-78-1.

"DPIHFP" or "DPIPF6" refers to diphenyliodonium hexafluorophosphate, CAS Reg. No. 58109-40-3, obtained from Johnson Matthey, Alfa Aesar Division (Ward Hill, Mass.).

"ENMAP" refers to ethyl N-methyl-N-phenyl-3-aminopropionate (also referred to as N-methyl-N-phenyl-beta-alanine ethyl ester), CAS Reg. No. 2003-76-1, which was prepared by the method described by Adamson, et al.; JCSOA9; J. Chem. Soc.; 1949; spl. 144-152, which is incorporated herein by reference.

"GENIOSIL GF-31" or "GF-31" refers to 3-methacryloxypropyltrimethoxysilane, obtaned from Wacker Chemie AG (Munich, Germany).

"IRGACURE 819" refers to a bis(2,4,6-trimethylbenzoyl) phenylphosphine oxide photoinitiator, CAS Reg. No. 162881-26-7, obtained from Ciba Specialty Chemicals Corporation, also available from the Sigma-Aldrich Corporation.

"PEG600 DM" refers to poly(ethylene glycol) dimethacrylate, average MW about 600, obtained from the Sartomer Company.

"TEGDMA" refers to triethyleneglycol dimethacrylate, CAS Reg. No. 109-16-0, obtained from the Sartomer Company.

"UDMA" refers to diurethane dimethacrylate, CAS Reg. No. 72869-86-4, obtained under the trade designation "ROHAMERE 6661-0" from Rohm America LLC (Piscataway, N.J.).

Fillers

"S/T Silica/Zirconia Nanoclusters" refers to silane-treated silica-zirconia nanocluster filler, prepared essentially as described in U.S. Pat. No. 6,730,156 at column 25, lines 50-63 (Preparatory Example A) and at column 25, line 64 through column 26, line 40 (Preparatory Example B) with minor modifications, including performing the silanization in 1-methoxy-2-propanol (rather than water) adjusted to a pH of about 8.8 with NH$_4$OH (rather than to a pH of 3-3.3 with trifluoroacetic acid), and obtaining the S/T Silica/Zirconia Nanoclusters by gap drying (rather than spray drying).

"S/T 20 nm Silica Nanoparticle" refers to silane-treated silica nanoparticle filler having a nominal particle size of approximately 20 nanometers, prepared essentially as described in U.S. Pat. No. 6,572,693 at column 21, lines 63-67 (Nano-sized particle filler, Type #2).

"S/T Nanozirconia Nanoparticle" refers to silane-treated zirconia nanoparticle filler, prepared from the zirconia sol as generally described in U.S. Pat. No. 8,647,510 at column 36 line 61 to column 37 line 16 (Example 11A-IER). The zirconia sol was added to an equivalent weight of 1-methoxy-2-propanol containing 3-methacryloxypropyltrimethoxysilane (1.1 mmol of 3-methacryloxypropyltrimethoxysilane per gram of nanozirconia to be surface treated). The mixture was heated to about 85° C. for 3 hours with stirring. The mixture was cooled to 35° C., adjusted to a pH of about 9.5 with NH$_4$OH, and the mixture reheated to about 85° C. for 4 hours with stirring. The resultant S/T Nanozirconia was isolated by removing solvents via gap drying. S/T Nanozirconia may also be prepared as described in U.S. Pat. No. 7,649,029 beginning at column 19, line 39 through column 20, line 41 (Filler I), except for the substitution of 3-methacryloxypropyltrimethoxysilane for the blend of Silquest A-174 and A-1230, and further removing the solvents via gap drying.

Ceramic Fibers
Ceramic Fibers A

Alumina-silicate ceramic fibers (mean diameter of 3.60 micrometers, available from Unifrax LLC (Niagara Falls, N.Y.) under the name "SAFFIL LDM" were chopped using an IKA 2870900 MF 10.1 Cutting-Grinding Head for Continuous-Feed Grinding Drive (available from Cole-Parmer, Vernon Hills, Ill.) operating at 3000 RPM. The chopped fibers were silane-treated by placing them in a solution of ethyl acetate, GF-31 silane (0.015 g per gram of fiber), and a 30% aqueous solution of ammonia (0.02 g per gram of fiber). Enough ethyl acetate was used to make the mixture flowable. The fibers were stirred for about 24 hours, removed from the solution, and then dried at 80° C. for about 1.5 hours to provide the Ceramic Fibers A.

The length of the chopped fibers was determined according to the method described above. The median length of the fibers was 153 micrometers. The mean length of the fibers was 198 micrometers (SD=141). With regard to distribution, 96% of the fibers were less than 500 micrometers in length and 64% of the fibers were less than 200 micrometers in length. The calculated ratio of mean fiber length to mean fiber diameter was 55.

Ceramic Fibers B

Alumina-silicate ceramic fibers (mean diameter of 4.70 micrometers, available from Unifrax LLC under the name "SAFFIL 3D+ Fiber"), were chopped using an IKA 2870900 MF 10.1 Cutting-Grinding Head for Continuous-Feed Grinding Drive operating at 3000 RPM. The chopped fibers were silane-treated by placing them in a solution of ethyl acetate, GF-31 silane (0.015 g per gram of fiber), and a 30% aqueous solution of ammonia (0.02 g per gram of fiber). Enough ethyl acetate was used to make the mixture flowable. The fibers were stirred for about 24 hours, removed from the solution, and then dried at 80° C. for about 1.5 hours to provide the Ceramic Fibers B.

The length of the chopped fibers was determined according to the method described above. The median length of the fibers was 59 micrometers. The mean length of the fibers was 88 micrometers (SD=59). With regard to distribution, all of the fibers were less than 500 micrometers in length and 85.6 of the fibers were less than 200 micrometers in length. The calculated ratio of mean fiber length to mean fiber diameter was 19.

Ceramic Fibers C

Glass fibers mean (mean diameter of 0.35 micrometers, available from the Johns Manville Company (Waterville, Ohio) under the name "JM MICRO-STRAND 106-475") were chopped using an IKA 2870900 MF 10.1 Cutting-Grinding Head for Continuous-Feed Grinding Drive operating at 3000 RPM. The chopped fibers were silane-treated by placing them in a solution of ethyl acetate, GF-31 silane (0.045 g per gram of fiber), and a 30% aqueous solution of ammonia (0.02 g per gram of fiber). Enough ethyl acetate was used to make the mixture flowable. The fibers were stirred for about 24 hours, removed from the solution, and then dried at 80° C. for about 1.5 hours to provide the Ceramic Fibers C.

The length of the chopped fibers was determined according to the method described above. The median length of the fibers was 34 micrometers. The mean length of the fibers was 48 micrometers (SD=38). With regard to distribution, all of the fibers were less than 500 micrometers in length and 99% of the fibers were less than 200 micrometers in length. The calculated ratio of mean fiber length to mean fiber diameter was 138.

Ceramic Fibers D

Glass fibers (mean diameter of 2.05 micrometers, available from the Johns Manville Company under the name "JM MICRO-STRAND 110X-481") were chopped using an IKA 2870900 MF 10.1 Cutting-Grinding Head for Continuous-Feed Grinding Drive operating at 3000 RPM. The chopped fibers were silane-treated by placing them in a solution of ethyl acetate, GF-31 silane (0.01 g per gram of fiber), and a 30% aqueous solution of ammonia (0.02 g per gram of fiber). Enough ethyl acetate was used to make the mixture flowable. The fibers were stirred for about 24 hours, removed from the solution, and then dried at 80° C. for about 1.5 hours to provide the Ceramic Fibers D.

The length of the chopped fibers was determined according to the method described above. The median length of the fibers was 42 micrometers. The mean length of the fibers was 57 micrometers (SD=55). With regard to distribution, all of the fibers were less than 500 micrometers in length and 94% of the fibers were less than 200 micrometers in length. The calculated ratio of mean fiber length to mean fiber diameter was 28.

Ceramic Fibers E

Ceramic alumina-silica fibers (mean diameter of 0.92 micrometers, available from Unifrax LLC under the name "FIBERFRAX Ceramic Fiber Bulk 7000") were chopped using an IKA 2870900 MF 10.1 Cutting-Grinding Head for Continuous-Feed Grinding Drive operating at 3000 RPM. The chopped fibers were silane-treated by placing them in a solution of ethyl acetate, GF-31 silane (0.01 g per gram of fiber), and a 30% aqueous solution of ammonia (0.02 g per gram of fiber). Enough ethyl acetate was used to make the mixture flowable. The fibers were stirred for about 24 hours, removed from the solution, and then dried at 80° C. for about 1.5 hours to provide the Ceramic Fibers E.

The length of the chopped fibers was determined according to the method described above. The median length of the fibers was 27 micrometers. The mean length of the fibers was 37 micrometers (SD=29) and all of the fibers were less than 200 micrometers in length. The calculated ratio of mean fiber length to mean fiber diameter was 40.

Ceramic Fibers F

Alumina-silicate ceramic fibers with 50% alumina and 50% silica by weight (diameter of 10-15 micrometers) were prepared by sol-gel methods as described in U.S. Pat. No. 4,047,965 at column 15 line 5 to column 16 line 55 (Example 1) with the modifications that the ratio of alumina to silica was one-to-one by weight, and the fibers were calcined to 1100° C. The fibers were chopped by hand using a razor blade on a rubber mat to produce fibers with a length of approximately 200 micrometers. The chopped fibers were silane-treated by placing them in a solution of ethyl acetate, GF-31 silane (0.01 g per gram of fiber), and a 30% aqueous solution of ammonia (0.02 g per gram of fiber). Enough ethyl acetate was used to make the mixture flowable. The fibers were stirred for about 24 hours, removed from the solution, and then dried at 80° C. for about 1.5 hours to provide the Ceramic Fibers F.

Ceramic Fibers G

Ceramic Fibers G were prepared by silane-treating #38 1/32 inch milled glass fibers (obtained from the Fibre Glast Developments Corporation, Brookville, Ohio). The fibers were reported by the manufacturer to have a mean diameter of 16 micrometers and a mean length of 230 micrometers. The fibers were silane-treated by placing them in a solution of ethyl acetate, GF-31 silane (0.01 g per gram of fiber), and a 30% aqueous solution of ammonia (0.02 g per gram of fiber). Enough ethyl acetate was used to make the mixture flowable. The fibers were stirred for about 24 hours and then dried at 80° C. for about 1.5 hours.

Ceramic Fibers H

Amorphous aluminoborosilicate ceramic fibers (available from the 3M Corporation under the name "NEXTEL 312 Ceramic Fiber", reported diameter of 10-12 micrometers) were chopped by Engineered Fibers Technology, LLC (Shelton, Conn.) to lengths of approximately 200 micrometers. The chopped fibers were silane-treated by placing them in a solution of ethyl acetate, GF-31 silane (0.01 g per gram of fiber), and a 30% aqueous solution of ammonia (0.02 g per gram of fiber). Enough ethyl acetate was used to make the mixture flowable. The fibers were stirred for about 24 hours, removed from the solution, and then dried at 80° C. for about 1.5 hours to provide the Ceramic Fibers H.

Ceramic Fibers I

Amorphous aluminoborosilicate ceramic fibers (available from the 3M Corporation under the name "NEXTEL 312 Ceramic Fiber", reported diameter of 10-12 micrometers) were chopped using an IKA 2870900 MF 10.1 Cutting-Grinding Head for Continuous-Feed Grinding Drive operating at 3000 RPM to lengths of approximately 200 micrometers. The chopped fibers were silane-treated by placing them in a solution of ethyl acetate, GF-31 silane (0.01 g per gram of fiber), and a 30% aqueous solution of ammonia (0.02 g per gram of fiber). Enough ethyl acetate was used to make the mixture flowable. The fibers were stirred for about 24 hours, removed from the solution, and then dried at 80° C. for about 1.5 hours to provide the Ceramic Fibers I.

Resin A

The polymerizable component, Resin A, was prepared by mixing the components shown in Table 1 until all the components were uniformly mixed.

TABLE 1

Formulation of Resin A

| Component | Weight Percent (wt. %) in the Resin Formulation |
|---|---|
| BisGMA | 24.575% |
| TEGDMA | 1.182% |
| UDMA | 34.401% |
| BisEMA-6 | 34.401% |
| PEG600DM | 3.736% |
| CPQ | 0.220% |
| DPIHFP | 0.350% |
| IRGACURE 819 | 0.050% |
| ENMAP | 0.810% |
| BHT | 0.150% |
| BZT | 0.125% |

Examples 1-9 and Comparative Examples A-E

Examples 1-9 (EX-1-EX-9) and Comparative Examples A-E (CE-A-CE-E) of composite materials were prepared by mixing the components shown in Tables 2-4 using a FlackTek model DAC150.1 FVZ high shear speed mixer (FlakTek Incorporated, Landrum, S.C.). The components were mixed to provide a uniform paste. Flexural Strength and Fracture Toughness of the composite materials were measured according to the procedures described above and the results are reported in Tables 5 and 6. Diametral Tensile Strength of the composite materials was measured according to the method described above and the results are reported in Table 7. Gloss Retention after Toothbrush Abrasion of the composite materials was determined according to the method described above and the results are reported in Tables 8 and 9.

TABLE 2

Composite Material Formulations for Examples 1-5 (EX-1-EX-5) containing Different Ceramic Fibers

| Components | EX-1 | EX-2 | EX-3 | EX-4 | EX-5 |
|---|---|---|---|---|---|
| Resin A (wt. %) | 20.0 | 20.0 | 24.0 | 24.0 | 22.0 |
| S/T Nanozirconia Nanoparticle (wt. %) | 4.2 | 4.2 | 4.0 | 4.0 | 4.1 |
| S/T 20 nm Silica Nanoparticle (wt. %) | 7.8 | 7.8 | 7.4 | 7.4 | 7.6 |
| S/T Silica/Zirconia Nanocluster (wt. %) | 51.0 | 51.0 | 48.4 | 48.4 | 49.7 |
| Ceramic Fibers A (wt. %) | 17.0 | 0 | 0 | 0 | 0 |
| Ceramic Fibers B (wt. %) | 0 | 17.0 | 0 | 0 | 0 |
| Ceramic Fibers C (wt. %) | 0 | 0 | 16.2 | 0 | 0 |
| Ceramic Fibers D (wt. %) | 0 | 0 | 0 | 16.2 | 0 |
| Ceramic Fibers E (wt. %) | 0 | 0 | 0 | 0 | 16.6 |

TABLE 3

Composite Material Formulations for Examples 6-9 (EX-6-EX-9)

| Components | EX-6 | EX-7 | EX-8 | EX-9 |
|---|---|---|---|---|
| Resin A (wt. %) | 20.0 | 20.0 | 24.0 | 24.0 |
| S/T Nanozirconia Nanoparticle (wt. %) | 4.2 | 4.2 | 4.0 | 4.0 |
| S/T 20 nm Silica Nanoparticle (wt. %) | 7.8 | 7.8 | 7.4 | 7.4 |

TABLE 3-continued

Composite Material Formulations for Examples 6-9 (EX-6-EX-9)

| Components | EX-6 | EX-7 | EX-8 | EX-9 |
|---|---|---|---|---|
| S/T Silica/Zirconia Nanocluster (wt. %) | 61.2 | 40.8 | 58.1 | 38.8 |
| Ceramic Fibers A (wt. %) | 6.8 | 27.2 | 0 | 0 |
| Ceramic Fibers C (wt. %) | 0 | 0 | 6.5 | 25.8 |

TABLE 4

Composite Material Formulations for Comparative Examples A-E (CE-A-CE-E) containing Different Ceramic Fibers

| Components | CE-A | CE-B | CE-C | CE-D | CE-E |
|---|---|---|---|---|---|
| Resin A (wt. %) | 22.0 | 20.5 | 24.0 | 24.0 | 22.0 |
| S/T Nanozirconia Nanoparticle (wt. %) | 4.1 | 4.0 | 4.2 | 4.2 | 4.2 |
| S/T 20 nm Silica Nanoparticle (wt. %) | 7.6 | 7.5 | 7.8 | 7.8 | 7.8 |
| S/T Silica/Zirconia Nanocluster (wt. %) | 66.3 | 49.5 | 51.0 | 51.0 | 51.0 |
| Ceramic Fibers F (wt. %) | 0 | 16.5 | 0 | 0 | 0 |
| Ceramic Fibers G (wt. %) | 0 | 0 | 17.0 | 0 | 0 |
| Ceramic Fibers H (wt. %) | 0 | 0 | 0 | 17.0 | 0 |
| Ceramic Fibers I (wt. %) | 0 | 0 | 0 | 0 | 17.0 |

TABLE 5

Mean Flexural Strength Measurements

| Example | Mean Flexural Strength (MPa) (n = 5) | Standard Deviation |
|---|---|---|
| EX-1 | 201.1 | 6.7 |
| EX-2 | 189.2 | 3.7 |
| EX-3 | 177.7 | 17.6 |
| EX-4 | 190.8 | 6.0 |
| EX-5 | 190.0 | 4.1 |
| EX-6 | 157.9 | 14.9 |
| EX-7 | 209.5 | 1.6 |
| EX-8 | 161.9 | 12.2 |
| EX-9 | 157.8 | 16.6 |
| CE-A | 150.8 | 6.3 |
| CE-B | 160.0 | 8.9 |
| CE-D | 156.2 | 5.1 |

TABLE 6

Mean Fracture Toughness Measurements

| Example | Mean Fracture Toughness (MPa · m$^{1/2}$) (n = 5) | Standard Deviation |
|---|---|---|
| EX-1 | 2.81 | 0.04 |
| EX-2 | 2.65 | 0.08 |
| EX-3 | 2.55 | 0.08 |
| EX-4 | 2.76 | 0.21 |
| EX-5 | 2.53 | 0.12 |
| EX-6 | 2.20 | 0.30 |
| EX-7 | 3.18 | 0.23 |
| EX-8 | 2.32 | 0.18 |
| EX-9 | 2.55 | 0.19 |
| CE-A | 1.92 | 0.13 |
| CE-B | 2.75 | 0.11 |
| CE-C | 2.27 | 0.08 |
| CE-D | 2.38 | 0.11 |

TABLE 7

Mean Diametral Tensile Strength Measurements

| Example | Mean Diametral Tensile Strength (MPa) (n = 9) | Standard Deviation |
|---|---|---|
| EX-1 | 72.1 | 2.0 |
| EX-2 | 69.4 | 2.6 |
| EX-3 | 76.4 | 2.7 |
| EX-4 | 71.1 | 4.9 |
| EX-5 | 74.7 | 5.2 |
| CE-A | 83.2 | 4.0 |
| CE-B | 54.0 | 4.2 |
| CE-C | 62.3 | 2.0 |
| CE-D | 69.1 | 1.2 |
| CE-E | 58.2 | 3.6 |

TABLE 8

Gloss Retention after Toothbrush Abrasion Measurements

| Example | Percentage of Ceramic Fibers A in Formulation | Mean Gloss Measurement following Brushing (with Standard Deviation) | | | | |
|---|---|---|---|---|---|---|
| | | 0 Brushes | 1500 Brushes | 3000 Brushes | 4500 Brushes | 6000 Brushes |
| EX-6 | 6.8 wt. % | 87.9 (1.3) | 65.7 (1.4) | 50.7 (5.7) | 51.6 (2.4) | 49.0 (1.5) |
| EX-1 | 17.0 wt. % | 86.3 (1.7) | 57.9 (2.1) | 49.1 (1.9) | 41.6 (0.7) | 31.9 (5.0) |
| EX-7 | 27.2 wt. % | 82.5 (2.4) | 47.6 (2.3) | 43.2 (1.3) | 34.3 (1.1) | 28.5 (1.4) |
| CE-A | 0 wt. % | 91.5 (4.8) | 78.5 (2.4) | 73.2 (2.2) | 72.3 (1.2) | 67.1 (1.1) |

TABLE 9

Gloss Retention after Toothbrush Abrasion Measurements

| Example | Percentage of Ceramic Fibers C in Formulation | Mean Gloss Measurement following Brushing (with Standard Deviation) | | | | |
|---|---|---|---|---|---|---|
| | | 0 Brushes | 1500 Brushes | 3000 Brushes | 4500 Brushes | 6000 Brushes |
| EX-8 | 6.5 wt. % | 94.1 (0.3) | 82.1 (0.9) | 79.6 (0.6) | 73.7 (1.9) | 72.6 (2.6) |
| EX-3 | 16.2 wt. % | 94.0 (0.3) | 71.3 (0.5) | 61.9 (1.1) | 51.7 (2.2) | 49.2 (2.1) |

TABLE 9-continued

Gloss Retention after Toothbrush Abrasion Measurements

| Example | Percentage of Ceramic Fibers C in Formulation | Mean Gloss Measurement following Brushing (with Standard Deviation) | | | | |
|---|---|---|---|---|---|---|
| | | 0 Brushes | 1500 Brushes | 3000 Brushes | 4500 Brushes | 6000 Brushes |
| EX-9 | 25.8 wt. % | 93.5 (0.9) | 69.3 (1.6) | 61.2 (5.1) | 53.1 (3.6) | 48.4 (4.2) |
| CE-A | 0 wt. % | 94.3 (0.5) | 83.8 (1.1) | 80.9.2 (1.1) | 77.2 (0.9) | 75.8 (0.7) |

All of the patents and patent applications mentioned above are hereby expressly incorporated by reference. In the event that any inconsistency exists between the disclosure of the present application and the disclosure(s) of any document incorporated herein by reference, the disclosure of the present application shall govern. The embodiments described above are illustrative of the present invention and other constructions are also possible. Accordingly, the present invention should not be deemed limited to the embodiments described in detail above and shown in the accompanying drawings, but instead only by a fair scope of the claims that follow along with their equivalents.

The invention claimed is:

1. A composite material, comprising:
   20 to 40 wt % of a polymerizable component;
   10 to 40 wt % of ceramic fibers selected from the group consisting of alumina fibers, alumina-silica fibers, zirconia-silica fibers, silicate fibers modified with alkali or alkaline earths, fused silica fibers, leached silica fibers, quartz fibers, and a combination thereof, or
   10 to 20 wt % of ceramic fibers selected from the group consisting of aluminum borosilicate fibers, borosilicate glass fibers, and a combination thereof; and
   30 to wt % of nanoclusters,
   wherein the: wt % values of the composite material are based on a total weight of the composite material and total to a value of 100 wt %, and
   wherein each of the ceramic fibers are characterized by a diameter and a length,
      the ceramic fibers have an arithmetic mean diameter of 0.3 micrometers to 5 micrometers, and
      the length of fifty percent of the ceramic fibers, based on a total number of the ceramic fibers, is at least 10 micrometers and less than 50 micrometers, and
      the length of ninety percent of the ceramic fibers, based on the total number of the ceramic fibers, is no greater than 500 micrometers, and
   wherein the composite material forms a hardened composite material, the hardened composite material is characterized by:
      a flexural strength of 170 MPa or greater, and
      a fracture toughness of 2.50 megapascals square root meters or greater.

2. The composite material of claim 1, wherein an aspect ratio of an arithmetic mean length of the ceramic fibers to the arithmetic mean diameter of the ceramic fibers is at least 10:1.

3. The composite material of claim 2, wherein the aspect ratio is up to 150:1.

4. The composite material of claim 1, wherein the arithmetic mean diameter is 0.3 to 3 micrometers or 2 to 5 micrometers.

5. The composite material of claim 1, wherein the length of ninety percent of the ceramic fibers, based on a total number of the ceramic fibers, is less than 200 micrometers.

6. The composite material of claim 1, further comprising up to 15 wt. % of nanoparticles.

7. The composite material of claim 1, wherein the polymerizable component forms a hardened polymerizable component, the hardened polymerizable component characterized by a refractive index,
   wherein the ceramic fibers are characterized by a refractive index, and
   wherein the refractive index of the ceramic fibers is a value within 0.1 or less of the refractive index of the hardened polymerizable component.

8. The composite material of claim 1, wherein the ceramic fibers are characterized by a refractive index value of 1.40 to 1.65.

9. The composite material of claim 1, the hardened composite material further characterized by one or more of:
   a diametral tensile strength of 65 megapascals or greater,
   a polish retention of 40 gloss units or greater at 60° after 6000 brush cycles, and
   a wear resistance ratio of 2.0 or less when comparing a wear resistance of the hardened composite material to a control composite material, wherein the control composite material is free of ceramic fibers.

10. The composite material of claim 1, wherein the length of fifty percent of the ceramic fibers is no greater than 42 micrometers.

11. The composite material of claim 1, the nanoclusters being silica-zirconia nanoclusters.

12. The composite material of claim 1, comprising:
   10 to 40 wt. % ceramic fibers selected from alumina fibers, alumina-silica fibers, zirconia-silica fibers, silicate fibers modified with alkali or alkaline earths, fused silica fibers, leached silica fibers, quartz fibers, and a combination thereof.

13. The composite material of claim 12, wherein the length of fifty percent of the ceramic fibers is no greater than 42 micrometers.

14. A composite material, comprising:
   20 to 40 wt % of a polymerizable component;
   6 to 40 wt % of ceramic fibers; and
   30 to 70 wt % of nanoclusters,
   wherein the wt % values of the composite material are based on a total weight of the composite material and total to a value of 100 wt %,
   wherein each of the ceramic fibers are characterized by a diameter and a length,
      the ceramic fibers have an arithmetic mean diameter of 0.3 micrometers to 5 micrometers, and
      the length of fifty percent of the ceramic fibers, based on a total number of the ceramic fibers, is at least 10 micrometers and less than 50 micrometers, and
      the length of ninety percent of the ceramic fibers, based on the total number of the ceramic fibers, is no greater than 500 micrometers, and
   wherein the composite material forms a hardened composite material, the hardened composite material characterized by one or more of:
   a diametral tensile strength of 65 megapascals or greater,
   a flexural strength of 170 MPa or greater,
   a fracture toughness of 2.50 megapascals·square root meters or greater,
   a polish retention of 40 gloss units or greater at 60° after 6000 brush cycles, and a wear-resistance ratio of 2.0 or less when comparing a wear resistance of the hardened composite material to a control composite material, wherein the control composite material is free of ceramic fibers.

15. A dental product made by hardening the composite material of claim 1.

16. The dental product of claim 15, wherein the dental product is selected from the group consisting of a dental restorative, a dental adhesive, a dental mill blank, a dental cement, a dental prostheses, an orthodontic device, an orthodontic adhesive, a dental casting material, artificial crowns, anterior fillings, posterior fillings, cavity liners, or a dental coating.

17. A method of making a composite material of claim 1, the method comprising:
   admixing the polymerizable component, the ceramic fibers, and the nanoclusters to make the composite material.

18. A method of using a composite material of claim 1, the method comprising:
   placing the composite material near or on a tooth surface;
   changing the shape of the composite material near or on the tooth surface; and
   hardening the composite material.

19. A kit comprising:
   a composite material of claim 1; and
   at least one container to hold the composite material.

20. The kit of claim 19, further comprising at least one dental component selected from the group of a cement, an adhesive, an abrasive, a polishing paste, an instrument, software, a mill, a CAD/CAM system, a composite, a porcelain, a stain, a bur, an impression material, and a dental mill blank.

* * * * *